United States Patent
Smith

(10) Patent No.: US 10,808,861 B2
(45) Date of Patent: *Oct. 20, 2020

(54) VALVE SYSTEM

(71) Applicant: Fresenius Medical Care Holdings, Inc., Waltham, MA (US)

(72) Inventor: Mark Forrest Smith, Longmont, CO (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/232,498

(22) Filed: Dec. 26, 2018

(65) Prior Publication Data

US 2019/0203848 A1    Jul. 4, 2019

Related U.S. Application Data

(63) Continuation of application No. 15/146,509, filed on May 4, 2016, now Pat. No. 10,197,180, which is a continuation of application No. 13/548,711, filed on Jul. 13, 2012, now Pat. No. 9,360,129, which is a (Continued)

(51) Int. Cl.
*F16K 31/08* (2006.01)
*A61M 1/16* (2006.01)

(52) U.S. Cl.
CPC ............ *F16K 31/082* (2013.01); *A61M 1/16* (2013.01); *A61M 2205/128* (2013.01)

(58) Field of Classification Search
CPC .. F16K 31/082; A61M 1/16; A61M 2204/128
See application file for complete search history.

(56) References Cited

U.S. PATENT DOCUMENTS

| 2,276,843 | A | 3/1942 | Hathaway |
| 2,328,381 | A | 8/1943 | Jaffe |
| 2,569,105 | A | 9/1951 | James |

(Continued)

FOREIGN PATENT DOCUMENTS

| CN | 2183771 Y | 11/1994 |
| CN | 1146728 | 4/1997 |

(Continued)

OTHER PUBLICATIONS

Timby et al., Introductory Medical-Surgical Nursing, Lippincott Williams Wilkins, Ninth Edition, Chapter 28, p. 433.

(Continued)

*Primary Examiner* — Eric Keasel
(74) *Attorney, Agent, or Firm* — Novel IP

(57) ABSTRACT

The present specification is directed to a valve that has an orifice closing member adjacent to an orifice through which fluid can flow, a displacement member having a first portion and a second portion, where the first portion is adjacent to the orifice closing member when the valve is in an open position, a first magnet and a second magnet where the first and second magnets are sufficiently proximate to the displacement member to exert a magnetic force on the displacement member, and an actuator for generating a magnetic field to move the displacement member toward the first magnet, cause the first portion to press against the orifice closing member, and cause the orifice closing member to close the orifice.

18 Claims, 6 Drawing Sheets

Related U.S. Application Data continuation of application No. 12/351,969, filed on Jan. 12, 2009, now Pat. No. 8,240,636.

(56) References Cited

U.S. PATENT DOCUMENTS

| | | | |
|---|---|---|---|
| 2,977,791 A | 4/1961 | Dubsky | |
| 3,200,591 A | 8/1965 | Ray | |
| 3,216,281 A | 11/1965 | Teichert | |
| 3,242,456 A | 3/1966 | Duncan | |
| 3,308,798 A | 3/1967 | Snider | |
| 3,388,803 A | 6/1968 | Scott | |
| 3,420,492 A * | 1/1969 | Ray | F16K 31/56 251/68 |
| 3,464,448 A | 9/1969 | Schmitz | |
| 3,511,469 A | 5/1970 | Bell | |
| 3,514,674 A * | 5/1970 | Ito | H01F 7/1872 361/194 |
| 3,597,124 A | 8/1971 | Adams | |
| 3,669,878 A | 6/1972 | Marantz | |
| 3,669,880 A | 6/1972 | Marantz | |
| 3,709,222 A | 1/1973 | De Vries | |
| 3,728,654 A | 4/1973 | Tada | |
| 3,746,175 A | 7/1973 | Markley | |
| 3,752,189 A | 8/1973 | Marr | |
| 3,803,913 A | 4/1974 | Tracer | |
| 3,814,376 A | 6/1974 | Reinicke | |
| 3,841,799 A | 10/1974 | Spinosa | |
| 3,850,835 A | 11/1974 | Marantz | |
| 3,884,808 A | 5/1975 | Scott | |
| 3,894,431 A | 7/1975 | Muston | |
| 3,902,490 A | 9/1975 | Jacobsen | |
| 3,918,037 A | 11/1975 | Hall | |
| 3,927,955 A | 12/1975 | Spinosa | |
| 3,946,731 A | 3/1976 | Lichtenstein | |
| 3,961,918 A | 6/1976 | Johnson | |
| 3,983,361 A | 9/1976 | Wild | |
| 3,989,622 A | 11/1976 | Marantz | |
| 3,989,625 A * | 11/1976 | Mason | A61M 1/3624 210/94 |
| 3,994,799 A | 11/1976 | Yao | |
| 4,000,072 A | 12/1976 | Sato | |
| 4,047,099 A | 9/1977 | Berger | |
| 4,071,444 A | 1/1978 | Ash | |
| 4,079,007 A | 3/1978 | Hutchisson | |
| 4,083,777 A | 4/1978 | Hutchisson | |
| 4,094,775 A | 6/1978 | Mueller | |
| 4,099,700 A | 7/1978 | Young | |
| 4,113,614 A | 9/1978 | Rollo | |
| 4,118,314 A | 10/1978 | Yoshida | |
| 4,155,852 A | 5/1979 | Fischel | |
| 4,159,748 A | 7/1979 | Staudinger | |
| 4,187,057 A | 2/1980 | Xanthopoulos | |
| 4,209,392 A | 6/1980 | Wallace | |
| 4,212,738 A | 7/1980 | Henne | |
| 4,247,393 A | 1/1981 | Wallace | |
| 4,253,493 A * | 3/1981 | English | F01L 9/04 137/625.18 |
| 4,259,985 A | 4/1981 | Bergmann | |
| 4,267,040 A | 5/1981 | Schael | |
| 4,269,708 A | 5/1981 | Bonomini | |
| 4,326,955 A | 4/1982 | Babb | |
| 4,348,283 A | 9/1982 | Ash | |
| 4,354,562 A | 10/1982 | Newman | |
| 4,368,737 A | 1/1983 | Ash | |
| 4,371,385 A | 2/1983 | Johnson | |
| 4,381,999 A | 5/1983 | Boucher | |
| 4,387,777 A | 6/1983 | Ash | |
| 4,390,073 A | 6/1983 | Rosen | |
| 4,397,189 A | 8/1983 | Johnson | |
| 4,397,519 A | 8/1983 | Cooney | |
| 4,402,694 A | 9/1983 | Ash | |
| 4,403,765 A * | 9/1983 | Fisher | F16K 31/082 137/625.65 |
| 4,403,984 A | 9/1983 | Ash | |
| 4,413,988 A | 11/1983 | Handt | |
| 4,430,098 A | 2/1984 | Bowman | |
| 4,436,620 A | 3/1984 | Bellotti | |
| 4,443,333 A | 4/1984 | Mahurkar | |
| 4,460,555 A | 7/1984 | Thompson | |
| 4,464,172 A | 8/1984 | Lichtenstein | |
| 4,466,804 A | 8/1984 | Hino | |
| 4,469,593 A | 9/1984 | Ishihara | |
| 4,477,342 A | 10/1984 | Allan | |
| 4,480,483 A | 11/1984 | McShane | |
| 4,498,902 A | 2/1985 | Ash | |
| 4,531,799 A | 7/1985 | Gray | |
| 4,535,637 A | 8/1985 | Feller | |
| 4,559,039 A | 12/1985 | Ash | |
| 4,563,170 A | 1/1986 | Aigner | |
| 4,581,141 A | 4/1986 | Ash | |
| 4,586,576 A | 5/1986 | Inoue | |
| 4,596,550 A | 6/1986 | Troutner | |
| 4,599,055 A | 7/1986 | Dykstra | |
| 4,606,826 A | 8/1986 | Sano | |
| 4,630,799 A | 12/1986 | Nolan | |
| 4,650,587 A | 3/1987 | Polak | |
| 4,661,246 A | 4/1987 | Ash | |
| 4,666,598 A | 5/1987 | Heath | |
| 4,680,122 A | 7/1987 | Barone | |
| 4,683,053 A | 7/1987 | Polaschegg | |
| 4,710,164 A | 12/1987 | Levin | |
| 4,731,072 A | 3/1988 | Aid | |
| 4,740,755 A | 4/1988 | Ogawa | |
| 4,750,705 A | 6/1988 | Zippe | |
| 4,762,618 A | 8/1988 | Gummesson | |
| 4,765,421 A | 8/1988 | Newton | |
| 4,765,907 A | 8/1988 | Scott | |
| 4,777,953 A | 10/1988 | Ash | |
| 4,802,540 A | 2/1989 | Grabovac | |
| 4,806,247 A | 2/1989 | Schoendorfer | |
| 4,808,089 A | 2/1989 | Buchholtz | |
| 4,815,547 A | 3/1989 | Dillon | |
| 4,823,597 A | 4/1989 | White | |
| 4,826,663 A | 5/1989 | Alberti | |
| 4,828,543 A | 5/1989 | Weiss | |
| 4,828,693 A | 5/1989 | Lindsay | |
| 4,831,884 A | 5/1989 | Drenthen | |
| 4,840,542 A | 6/1989 | Abbott | |
| 4,854,322 A | 8/1989 | Ash | |
| 4,861,242 A | 8/1989 | Finsterwald | |
| 4,881,839 A | 11/1989 | Grimm | |
| 4,882,937 A | 11/1989 | Leon | |
| 4,885,942 A | 12/1989 | Magori | |
| 4,894,164 A | 1/1990 | Polaschegg | |
| 4,897,189 A | 1/1990 | Greenwood | |
| 4,909,713 A | 3/1990 | Finsterwald | |
| 4,914,819 A | 4/1990 | Ash | |
| 4,931,777 A | 6/1990 | Chiang | |
| 4,943,279 A | 7/1990 | Samiotes | |
| 4,950,244 A | 8/1990 | Fellingham | |
| 4,950,395 A | 8/1990 | Richalley | |
| 4,968,422 A | 11/1990 | Runge | |
| 4,985,015 A | 1/1991 | Obermann | |
| 4,990,258 A | 2/1991 | Bjare | |
| 4,994,035 A | 2/1991 | Mokros | |
| 4,995,268 A | 2/1991 | Ash | |
| 4,997,570 A | 3/1991 | Polaschegg | |
| 5,000,274 A | 3/1991 | Bullivant | |
| 5,002,054 A | 3/1991 | Ash | |
| 5,009,101 A | 4/1991 | Branam | |
| 5,011,607 A | 4/1991 | Shinzato | |
| 5,024,586 A | 6/1991 | Meiri | |
| 5,032,261 A | 7/1991 | Pyper | |
| 5,074,368 A | 12/1991 | Bullivant | |
| 5,100,554 A | 3/1992 | Polaschegg | |
| 5,114,580 A | 5/1992 | Ahmad | |
| 5,138,138 A | 8/1992 | Theilacker | |
| 5,147,613 A | 9/1992 | Heilmann | |
| 5,152,174 A | 10/1992 | Labudde | |
| 5,157,332 A | 10/1992 | Reese | |
| 5,161,779 A | 11/1992 | Graner | |
| 5,170,789 A | 12/1992 | Narayan | |

(56) References Cited

U.S. PATENT DOCUMENTS

| | | | |
|---|---|---|---|
| 5,188,604 A * | 2/1993 | Orth | A61M 1/10 128/DIG. 13 |
| 5,198,335 A | 3/1993 | Sekikawa | |
| 5,211,643 A | 5/1993 | Reinhardt | |
| 5,215,450 A | 6/1993 | Tamari | |
| 5,220,843 A | 6/1993 | Rak | |
| 5,228,308 A | 7/1993 | Day | |
| 5,230,341 A | 7/1993 | Polaschegg | |
| 5,230,614 A | 7/1993 | Zanger | |
| 5,258,127 A | 11/1993 | Gsell | |
| 5,259,961 A | 11/1993 | Eigendorf | |
| 5,277,820 A | 1/1994 | Ash | |
| 5,284,470 A | 2/1994 | Beltz | |
| 5,284,559 A | 2/1994 | Lim | |
| 5,295,505 A | 3/1994 | Polaschegg | |
| 5,304,114 A | 4/1994 | Cosman | |
| 5,304,349 A | 4/1994 | Polaschegg | |
| 5,308,315 A | 5/1994 | Khuri | |
| 5,322,258 A | 6/1994 | Bosch | |
| 5,322,519 A | 6/1994 | Ash | |
| 5,336,165 A | 8/1994 | Twardowski | |
| 5,339,699 A | 8/1994 | Carignan | |
| 5,346,472 A | 9/1994 | Keshaviah | |
| 5,347,115 A | 9/1994 | Sherman | |
| 5,352,364 A | 10/1994 | Kruger | |
| 5,360,445 A | 11/1994 | Goldowsky | |
| 5,385,005 A | 1/1995 | Ash | |
| D355,816 S | 2/1995 | Ash | |
| 5,391,143 A | 2/1995 | Kensey | |
| 5,405,315 A | 4/1995 | Khuri | |
| 5,405,320 A | 4/1995 | Twardowski | |
| 5,408,576 A | 4/1995 | Bishop | |
| 5,415,532 A | 5/1995 | Loughnane | |
| 5,441,636 A | 8/1995 | Chevallet | |
| 5,445,630 A | 8/1995 | Richmond | |
| 5,460,493 A | 10/1995 | Deniega | |
| 5,468,388 A | 11/1995 | Goddard | |
| 5,469,737 A | 11/1995 | Smith | |
| 5,476,444 A | 12/1995 | Keeling | |
| 5,518,015 A | 5/1996 | Berget | |
| D370,531 S | 6/1996 | Ash | |
| 5,536,412 A | 7/1996 | Ash | |
| 5,540,265 A | 7/1996 | Polaschegg | |
| 5,545,131 A | 8/1996 | Davankov | |
| 5,577,891 A | 11/1996 | Loughnane | |
| 5,580,460 A | 12/1996 | Polaschegg | |
| 5,591,344 A | 1/1997 | Kenley | |
| 5,609,770 A | 3/1997 | Zimmerman | |
| 5,614,677 A | 3/1997 | Wamsiedler | |
| 5,629,871 A | 3/1997 | Love | |
| 5,616,305 A | 4/1997 | Mathieu | |
| 5,624,551 A | 4/1997 | Baumann | |
| 5,624,572 A | 4/1997 | Larson | |
| 5,632,897 A | 5/1997 | Mathieu | |
| 5,644,285 A | 7/1997 | Maurer | |
| 5,647,853 A | 7/1997 | Feldmann | |
| 5,650,704 A | 7/1997 | Pratt | |
| 5,674,390 A | 10/1997 | Matthews | |
| 5,679,245 A | 10/1997 | Manica | |
| 5,685,835 A | 11/1997 | Brugger | |
| 5,690,821 A | 11/1997 | Kenley | |
| 5,693,008 A | 12/1997 | Brugger | |
| 5,695,473 A | 12/1997 | Olsen | |
| 5,698,083 A | 12/1997 | Glass | |
| 5,711,883 A | 1/1998 | Folden | |
| 5,713,850 A | 2/1998 | Heilmann | |
| 5,725,773 A | 3/1998 | Polaschegg | |
| 5,725,776 A | 3/1998 | Kenley | |
| 5,744,027 A | 4/1998 | Connell | |
| 5,760,313 A | 6/1998 | Guentner | |
| 5,762,782 A | 6/1998 | Kenley | |
| 5,765,591 A | 6/1998 | Wasson | |
| 5,770,806 A | 6/1998 | Hiismaeki | |
| 5,782,796 A | 7/1998 | Din | |
| 5,794,669 A | 8/1998 | Polaschegg | |
| 5,840,068 A | 11/1998 | Cartledge | |
| 5,858,186 A | 1/1999 | Glass | |
| 5,876,419 A | 3/1999 | Carpenter | |
| 5,902,336 A | 5/1999 | Mishkin | |
| 5,906,978 A | 5/1999 | Ash | |
| 5,919,369 A | 7/1999 | Ash | |
| 5,928,177 A | 7/1999 | Brugger | |
| 5,938,938 A | 8/1999 | Bosetto | |
| 5,944,684 A | 8/1999 | Roberts | |
| 5,945,343 A | 8/1999 | Munkholm | |
| 5,947,953 A | 9/1999 | Ash | |
| 5,951,870 A | 9/1999 | Utterberg | |
| 5,980,481 A | 11/1999 | Gorsuch | |
| 5,984,891 A | 11/1999 | Keilman | |
| 5,989,423 A | 11/1999 | Kamen | |
| 5,989,438 A | 11/1999 | Fumiyama | |
| 6,012,342 A | 1/2000 | Blight | |
| 6,042,561 A | 3/2000 | Ash | |
| 6,044,691 A | 4/2000 | Kenley | |
| 6,047,108 A | 4/2000 | Sword | |
| 6,062,256 A | 5/2000 | Miller | |
| 6,069,343 A | 5/2000 | Kolowich | |
| 6,086,753 A | 7/2000 | Ericson | |
| 6,116,269 A | 9/2000 | Maxson | |
| 6,117,100 A | 9/2000 | Powers | |
| 6,117,122 A | 9/2000 | Din | |
| 6,118,082 A | 9/2000 | Bissette | |
| 6,121,555 A | 9/2000 | Nowosielski | |
| 6,156,007 A | 12/2000 | Ash | |
| 6,168,578 B1 | 1/2001 | Diamond | |
| 6,187,199 B1 | 2/2001 | Goldau | |
| 6,190,349 B1 | 2/2001 | Ash | |
| 6,196,922 B1 | 3/2001 | Hantschk | |
| 6,196,992 B1 | 3/2001 | Keilman | |
| 6,200,485 B1 | 3/2001 | Kitaevich | |
| 6,217,540 B1 | 4/2001 | Yazawa | |
| 6,228,047 B1 | 5/2001 | Dadson | |
| 6,234,989 B1 | 5/2001 | Brierton | |
| 6,240,789 B1 | 6/2001 | Morlan | |
| 6,254,567 B1 | 7/2001 | Treu | |
| 6,264,611 B1 | 7/2001 | Ishikawa | |
| 6,264,680 B1 | 7/2001 | Ash | |
| 6,280,406 B1 | 8/2001 | Dolcek | |
| 6,284,131 B1 | 9/2001 | Hogard | |
| 6,287,516 B1 | 9/2001 | Matson | |
| 6,289,749 B1 | 9/2001 | Sanders | |
| 6,303,036 B1 | 10/2001 | Collins | |
| 6,325,774 B1 | 12/2001 | Bene | |
| 6,332,985 B1 | 12/2001 | Sherman | |
| 6,341,758 B1 | 1/2002 | Shih | |
| 6,348,162 B1 | 2/2002 | Ash | |
| 6,354,565 B1 * | 3/2002 | Doust | F16K 1/36 251/175 |
| 6,406,631 B1 | 6/2002 | Collins | |
| 6,409,699 B1 | 6/2002 | Ash | |
| 6,416,293 B1 | 7/2002 | Bouchard | |
| 6,468,427 B1 | 10/2002 | Frey | |
| 6,471,872 B2 | 10/2002 | Kitaevich | |
| 6,487,904 B1 | 12/2002 | Myhre | |
| 6,491,656 B1 | 12/2002 | Morris | |
| 6,491,673 B1 | 12/2002 | Palumbo | |
| 6,497,675 B1 | 12/2002 | Davankov | |
| 6,517,044 B1 | 2/2003 | Lin | |
| 6,517,045 B1 | 2/2003 | Northedge | |
| 6,551,513 B2 | 4/2003 | Nikaido | |
| 6,554,789 B1 | 4/2003 | Brugger | |
| 6,561,997 B1 | 5/2003 | Weitzel | |
| 6,565,395 B1 | 5/2003 | Schwarz | |
| 6,572,576 B2 | 6/2003 | Brugger | |
| 6,572,641 B2 | 6/2003 | Brugger | |
| 6,579,253 B1 | 6/2003 | Burbank | |
| 6,579,460 B1 | 6/2003 | Willis | |
| 6,582,385 B2 | 6/2003 | Burbank | |
| 6,589,482 B1 | 7/2003 | Burbank | |
| 6,595,943 B1 | 7/2003 | Burbank | |
| 6,607,495 B1 | 8/2003 | Skalak | |
| 6,610,036 B2 | 8/2003 | Branch | |
| 6,623,470 B2 | 9/2003 | Munis | |
| 6,627,164 B1 | 9/2003 | Wong | |

(56) References Cited

U.S. PATENT DOCUMENTS

| | | |
|---|---|---|
| 6,632,192 B2 | 10/2003 | Gorsuch |
| 6,638,477 B1 | 10/2003 | Treu |
| 6,638,478 B1 | 10/2003 | Treu |
| 6,649,063 B2 | 11/2003 | Brugger |
| 6,653,841 B1 | 11/2003 | Koerdt |
| 6,673,314 B1 | 1/2004 | Burbank |
| 6,681,624 B2 | 1/2004 | Furuki |
| 6,685,664 B2 | 2/2004 | Levin |
| 6,690,280 B2 | 2/2004 | Citrenbaum |
| 6,695,803 B1 | 2/2004 | Robinson |
| 6,702,561 B2 | 3/2004 | Stillig |
| 6,706,007 B2 | 3/2004 | Gelfand |
| 6,730,266 B2 | 5/2004 | Matson |
| 6,743,193 B2 | 6/2004 | Brugger |
| 6,752,172 B2 | 6/2004 | Lauer |
| 6,758,975 B2 | 7/2004 | Peabody |
| 6,764,460 B2 | 7/2004 | Dolecek |
| 6,773,412 B2 | 8/2004 | OMahony |
| 6,776,912 B2 | 8/2004 | Baurmeister |
| 6,796,955 B2 | 9/2004 | OMahony |
| 6,818,196 B2 | 11/2004 | Wong |
| 6,830,553 B1 | 12/2004 | Burbank |
| 6,836,201 B1 | 12/2004 | Devenyi |
| 6,841,172 B1 | 1/2005 | Ash |
| 6,843,779 B1 | 1/2005 | Andrysiak |
| 6,852,090 B2 | 2/2005 | Burbank |
| 6,872,346 B2 | 3/2005 | Stillig |
| 6,878,283 B2 | 4/2005 | Thompson |
| 6,886,801 B2 * | 5/2005 | Hallback ............... F16K 31/082 251/129.15 |
| 6,890,315 B1 | 5/2005 | Levin |
| 6,899,691 B2 | 5/2005 | Bainbridge |
| 6,923,782 B2 | 8/2005 | Omahony |
| 6,948,697 B2 | 9/2005 | Herbert |
| 6,955,655 B2 | 10/2005 | Burbank |
| 6,958,049 B1 | 10/2005 | Ash |
| 6,960,179 B2 | 11/2005 | Gura |
| 6,960,328 B2 | 11/2005 | Bortun |
| 6,979,309 B2 | 12/2005 | Burbank |
| 7,004,924 B1 | 2/2006 | Brugger |
| 7,007,549 B2 | 3/2006 | Kwon |
| 7,033,498 B2 | 4/2006 | Wong |
| 7,037,428 B1 | 5/2006 | Robinson |
| 7,040,142 B2 | 5/2006 | Burbank |
| 7,059,195 B1 | 6/2006 | Liu |
| 7,087,026 B2 | 8/2006 | Callister |
| 7,087,033 B2 | 8/2006 | Brugger |
| 7,097,148 B2 | 8/2006 | DeWall |
| 7,101,519 B2 | 9/2006 | Wong |
| 7,112,273 B2 | 9/2006 | Weigel |
| 7,115,095 B2 | 10/2006 | Egler |
| 7,135,156 B2 | 11/2006 | Hai |
| 7,144,386 B2 | 12/2006 | Korkor |
| 7,146,861 B1 | 12/2006 | Cook |
| 7,147,613 B2 | 12/2006 | Burbank |
| 7,169,303 B2 | 1/2007 | Sullivan |
| 7,175,809 B2 | 2/2007 | Gelfand |
| 7,214,312 B2 | 5/2007 | Brugger |
| 7,226,538 B2 | 6/2007 | Brugger |
| 7,241,272 B2 | 7/2007 | Karoor |
| 7,252,767 B2 | 8/2007 | Bortun |
| 7,267,658 B2 | 9/2007 | Treu |
| 7,270,015 B1 | 9/2007 | Feller |
| 7,273,465 B2 | 9/2007 | Ash |
| 7,276,042 B2 | 10/2007 | Polaschegg |
| 7,300,413 B2 | 11/2007 | Burbank |
| 7,309,323 B2 | 12/2007 | Gura |
| 7,314,208 B1 | 1/2008 | Rightley |
| 7,317,967 B2 | 1/2008 | DiGianfilippo |
| 7,332,096 B2 | 2/2008 | Blickhan |
| 7,337,674 B2 | 3/2008 | Burbank |
| 7,338,460 B2 | 3/2008 | Burbank |
| 7,347,849 B2 | 3/2008 | Brugger |
| 7,351,218 B2 | 4/2008 | Bene |
| 7,387,022 B1 | 6/2008 | Korniyenko |
| 7,494,590 B2 | 2/2009 | Felding |
| 7,531,098 B2 | 5/2009 | Robinson |
| 7,566,432 B2 | 7/2009 | Wong |
| 7,597,677 B2 | 10/2009 | Gura |
| 7,605,710 B2 | 10/2009 | Crnkovich |
| 7,618,531 B2 | 11/2009 | Sugioka |
| 7,628,378 B2 | 12/2009 | Adams |
| 7,645,253 B2 | 1/2010 | Gura |
| 7,648,476 B2 | 1/2010 | Bock |
| 7,696,762 B2 | 4/2010 | Quackenbush |
| 7,713,226 B2 | 5/2010 | Ash |
| 7,736,507 B2 | 6/2010 | Wong |
| 7,755,488 B2 | 7/2010 | Dvorsky |
| 7,766,873 B2 | 8/2010 | Moberg |
| 7,776,210 B2 | 8/2010 | Rosenbaum |
| 7,780,619 B2 | 8/2010 | Brugger |
| 7,794,141 B2 | 9/2010 | Perry |
| 7,861,740 B2 | 1/2011 | Phallen |
| 7,873,489 B2 | 1/2011 | Dolgos |
| 7,874,999 B2 | 1/2011 | Busby |
| 7,886,611 B2 | 2/2011 | OMahony |
| 7,896,829 B2 | 3/2011 | Gura |
| 7,901,376 B2 | 3/2011 | Steck |
| 7,914,477 B2 | 3/2011 | Briggs |
| 7,922,898 B2 | 4/2011 | Jonsson |
| 7,922,899 B2 | 4/2011 | Vasta |
| 7,935,074 B2 | 5/2011 | Plahey |
| 7,959,129 B2 | 6/2011 | Matsumoto |
| 7,981,082 B2 | 7/2011 | Wang |
| 7,981,280 B2 | 7/2011 | Carr |
| 7,995,816 B2 | 8/2011 | Roger |
| 7,998,101 B2 | 8/2011 | Ash |
| 8,021,319 B2 | 9/2011 | Delnevo |
| 8,029,454 B2 | 10/2011 | Kelly |
| 8,034,161 B2 | 10/2011 | Gura |
| 8,034,235 B2 | 10/2011 | Rohde |
| 8,062,513 B2 | 11/2011 | Yu |
| 8,066,658 B2 | 11/2011 | Karoor |
| 8,070,707 B2 | 12/2011 | Gelfand |
| 8,075,509 B2 | 12/2011 | Molducci |
| 8,078,333 B2 | 12/2011 | Kienman |
| 8,083,677 B2 | 12/2011 | Rohde |
| 8,105,260 B2 | 1/2012 | Tonelli |
| 8,105,487 B2 | 1/2012 | Fulkerson |
| 8,114,288 B2 | 2/2012 | Robinson |
| 8,118,276 B2 | 2/2012 | Sanders |
| 8,123,947 B2 | 2/2012 | Rohde |
| 8,152,751 B2 | 2/2012 | Roger |
| 8,142,383 B2 | 3/2012 | Dannenmaier |
| 8,187,184 B2 | 5/2012 | Muller |
| 8,192,401 B2 | 6/2012 | Morris |
| 8,197,431 B2 | 6/2012 | Bennison |
| 8,206,338 B2 | 6/2012 | Childers |
| 8,210,493 B2 | 7/2012 | Miyagawa |
| 8,221,320 B2 | 7/2012 | Bouton |
| 8,240,636 B2 * | 8/2012 | Smith ................... F16K 31/082 251/129.19 |
| 8,273,049 B2 | 9/2012 | Demers |
| 8,316,725 B2 | 11/2012 | Wade |
| 8,323,492 B2 | 12/2012 | Childers |
| 8,342,478 B1 | 1/2013 | Cordray |
| 8,376,978 B2 | 2/2013 | Roger |
| 8,449,487 B2 | 5/2013 | Hovland |
| 8,491,184 B2 | 7/2013 | Kamen |
| 8,597,505 B2 * | 12/2013 | Fulkerson ............... B01D 61/32 210/86 |
| 8,622,365 B2 | 1/2014 | Fukano |
| 8,696,626 B2 | 4/2014 | Kirsch |
| 9,308,307 B2 | 4/2016 | Fulkerson |
| 9,354,640 B2 | 5/2016 | Byler |
| 9,360,129 B2 * | 6/2016 | Smith ................... F16K 31/082 |
| 9,517,296 B2 | 12/2016 | Fulkerson |
| 1,001,902 A1 | 7/2018 | Byler |
| 1,025,873 A1 | 4/2019 | Fulkerson |
| 2001/0038083 A1 | 11/2001 | Sakurai |
| 2002/0050412 A1 | 5/2002 | Emery |
| 2002/0068364 A1 | 6/2002 | Arai |
| 2002/0085951 A1 | 7/2002 | Gelfand |
| 2002/0112609 A1 | 8/2002 | Wong |

(56) References Cited

U.S. PATENT DOCUMENTS

| | | |
|---|---|---|
| 2002/0113016 A1 | 8/2002 | Takai |
| 2002/0139419 A1 | 10/2002 | Flinchbaugh |
| 2002/0147423 A1 | 10/2002 | Burbank |
| 2002/0158019 A1 | 10/2002 | Collins |
| 2002/0187069 A1 | 12/2002 | Levin |
| 2002/0193679 A1 | 12/2002 | Malave |
| 2003/0001590 A1 | 1/2003 | Mengle |
| 2003/0012905 A1 | 1/2003 | Zumbrum |
| 2003/0042181 A1 | 3/2003 | Metzner |
| 2003/0048185 A1 | 3/2003 | Citrenbaum |
| 2003/0056585 A1 | 3/2003 | Furuki |
| 2003/0113931 A1 | 6/2003 | Pan |
| 2003/0113932 A1 | 6/2003 | Sternberg |
| 2003/0128125 A1 | 7/2003 | Burbank |
| 2003/0216677 A1 | 11/2003 | Pan |
| 2003/0220598 A1 | 11/2003 | Busby |
| 2003/0220606 A1 | 11/2003 | Busby |
| 2003/0236482 A1 | 12/2003 | Gorsuch |
| 2004/0018100 A1 | 1/2004 | Takagi |
| 2004/0019312 A1 | 1/2004 | Childers |
| 2004/0021108 A1 | 2/2004 | Hallback |
| 2004/0031756 A1 | 2/2004 | Suzuki |
| 2004/0167465 A1 | 8/2004 | Mihai |
| 2004/0195055 A1 | 10/2004 | Gilles |
| 2005/0006296 A1 | 1/2005 | Sullivan |
| 2005/0010190 A1 | 1/2005 | Yeakley |
| 2005/0045548 A1 | 3/2005 | Brugger |
| 2005/0070837 A1 | 3/2005 | Ferrarini |
| 2005/0086008 A1 | 4/2005 | Digianfilippo |
| 2005/0092079 A1 | 5/2005 | Ales |
| 2005/0101901 A1 | 5/2005 | Gura |
| 2005/0113734 A1 | 5/2005 | Brugger |
| 2005/0131332 A1 | 6/2005 | Kelly |
| 2005/0133439 A1 | 6/2005 | Blickhan |
| 2005/0150309 A1 | 7/2005 | Beard |
| 2005/0209547 A1 | 9/2005 | Burbank |
| 2005/0230292 A1 | 10/2005 | Beden |
| 2005/0240233 A1 | 10/2005 | Lippert |
| 2006/0064053 A1 | 3/2006 | Bollish |
| 2006/0091056 A1 | 5/2006 | Brugger |
| 2006/0113249 A1 | 6/2006 | Childers |
| 2006/0117859 A1 | 6/2006 | Liu |
| 2006/0122552 A1 | 6/2006 | OMahony |
| 2006/0195064 A1 | 8/2006 | Plahey |
| 2006/0226057 A1 | 10/2006 | Robinson |
| 2006/0226090 A1 | 10/2006 | Robinson |
| 2006/0241543 A1 | 10/2006 | Gura |
| 2006/0289342 A1 | 12/2006 | Sugioka |
| 2007/0060786 A1 | 3/2007 | Gura |
| 2007/0088333 A1 | 4/2007 | Levin |
| 2007/0112297 A1 | 5/2007 | Plahey |
| 2007/0158249 A1 | 7/2007 | Ash |
| 2007/0158268 A1 | 7/2007 | DeComo |
| 2007/0161113 A1 | 7/2007 | Ash |
| 2007/0179425 A1 | 8/2007 | Gura |
| 2007/0213654 A1 | 9/2007 | Lundtveit |
| 2007/0253463 A1 | 11/2007 | Perry |
| 2007/0276328 A1 | 11/2007 | Childers |
| 2008/0006570 A1 | 1/2008 | Gura |
| 2008/0021366 A1 | 1/2008 | Gura |
| 2008/0041136 A1 | 2/2008 | Kopelman |
| 2008/0041792 A1 | 2/2008 | Crnkovich |
| 2008/0051689 A1 | 2/2008 | Gura |
| 2008/0058696 A1 | 3/2008 | Gura |
| 2008/0065006 A1 | 3/2008 | Roger |
| 2008/0077068 A1 | 3/2008 | Orr |
| 2008/0149563 A1 | 6/2008 | Ash |
| 2008/0195021 A1 | 8/2008 | Roger |
| 2008/0195060 A1 | 8/2008 | Roger |
| 2008/0208103 A1 | 8/2008 | Demers |
| 2008/0217245 A1 | 9/2008 | Rambod |
| 2008/0230450 A1 | 9/2008 | Burbank |
| 2008/0258735 A1 | 10/2008 | Quackenbush |
| 2008/0264498 A1 | 10/2008 | Thompson |
| 2008/0290974 A1 | 11/2008 | Adams |
| 2009/0004053 A1 | 1/2009 | Kenley |
| 2009/0008306 A1 | 1/2009 | Cicchello |
| 2009/0008331 A1 | 1/2009 | Wilt |
| 2009/0010627 A1 | 1/2009 | Lindsay |
| 2009/0076434 A1 | 3/2009 | Mischelevich |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0083331 A1 | 3/2009 | Oh |
| 2009/0095679 A1 | 4/2009 | Demers |
| 2009/0101549 A1 | 4/2009 | Kamen |
| 2009/0101552 A1 | 4/2009 | Fulkerson |
| 2009/0101577 A1 | 4/2009 | Fulkerson |
| 2009/0105627 A1 | 4/2009 | Rohde |
| 2009/0107902 A1 | 4/2009 | Childers |
| 2009/0112155 A1 | 4/2009 | Zhao |
| 2009/0112507 A1 | 4/2009 | Edney |
| 2009/0113335 A1 | 4/2009 | Sandoe |
| 2009/0114037 A1 | 5/2009 | Smith |
| 2009/0120864 A1 | 5/2009 | Fulkerson |
| 2009/0124963 A1 | 5/2009 | Hogard |
| 2009/0127193 A1 | 5/2009 | Updyke |
| 2009/0127793 A1 | 5/2009 | Ferris |
| 2009/0137940 A1 | 5/2009 | Orr |
| 2009/0173682 A1 | 7/2009 | Robinson |
| 2009/0282980 A1 | 11/2009 | Gura |
| 2009/0312694 A1 | 12/2009 | Bedingfield |
| 2010/0022936 A1 | 1/2010 | Gura |
| 2010/0078381 A1 | 4/2010 | Merchant |
| 2010/0078387 A1 | 4/2010 | Wong |
| 2010/0084330 A1 | 4/2010 | Wong |
| 2010/0094193 A1 | 4/2010 | Gura |
| 2010/0100034 A1 | 4/2010 | Wich-Heiter |
| 2010/0101664 A1 | 4/2010 | Yamamoto |
| 2010/0116048 A1 | 5/2010 | Fulkerson |
| 2010/0116740 A1 | 5/2010 | Fulkerson |
| 2010/0129247 A1 | 5/2010 | Lauer |
| 2010/0133153 A1 | 6/2010 | Beden |
| 2010/0140149 A1 | 6/2010 | Fulkerson |
| 2010/0179464 A1 | 7/2010 | Smith |
| 2010/0184198 A1 | 7/2010 | Joseph |
| 2010/0192686 A1 | 8/2010 | Kamen |
| 2010/0209300 A1 | 8/2010 | Dirac |
| 2010/0234786 A1 | 9/2010 | Fulkerson |
| 2010/0252490 A1 | 10/2010 | Fulkerson |
| 2010/0312161 A1 | 12/2010 | Jonsson |
| 2010/0326911 A1 | 12/2010 | Rosenbaum |
| 2010/0326916 A1 | 12/2010 | Wrazel |
| 2010/0331754 A1 | 12/2010 | Fulkerson |
| 2011/0000830 A1 | 1/2011 | Ikeda |
| 2011/0000832 A1 | 1/2011 | Kelly |
| 2011/0009799 A1 | 1/2011 | Mullick |
| 2011/0017665 A1 | 1/2011 | Updyke |
| 2011/0028881 A1 | 2/2011 | Basaglia |
| 2011/0028882 A1 | 2/2011 | Basaglia |
| 2011/0041928 A1 | 2/2011 | Volker |
| 2011/0046533 A1 | 2/2011 | Stefani |
| 2011/0054352 A1 | 3/2011 | Ko |
| 2011/0054378 A1 | 3/2011 | Fulkerson |
| 2011/0071465 A1 | 3/2011 | Wang |
| 2011/0083746 A1 | 4/2011 | Hoang |
| 2011/0087187 A1 | 4/2011 | Beck |
| 2011/0092907 A1 | 4/2011 | Krogh |
| 2011/0093294 A1 | 4/2011 | Elahi |
| 2011/0098545 A1 | 4/2011 | Ross |
| 2011/0098624 A1 | 4/2011 | McCotter |
| 2011/0098625 A1 | 4/2011 | Masala |
| 2011/0098635 A1 | 4/2011 | Helmore |
| 2011/0105877 A1 | 5/2011 | Wilt |
| 2011/0105981 A1 | 5/2011 | Wagner |
| 2011/0105983 A1 | 5/2011 | Kelly |
| 2011/0105984 A1 | 5/2011 | Patel |
| 2011/0106002 A1 | 5/2011 | Helmore |
| 2011/0106047 A1 | 5/2011 | Burbank |
| 2011/0106466 A1 | 5/2011 | Furmanksi |

(56) References Cited

U.S. PATENT DOCUMENTS

| | | |
|---|---|---|
| 2011/0107251 A1 | 5/2011 | Guaitoli |
| 2011/0108482 A1 | 5/2011 | Lovell |
| 2011/0125073 A1 | 5/2011 | Rambod |
| 2011/0126714 A1 | 6/2011 | Brugger |
| 2011/0132838 A1 | 6/2011 | Curtis |
| 2011/0132841 A1 | 6/2011 | Rohde |
| 2011/0137224 A1 | 6/2011 | Ibragimov |
| 2011/0137264 A1 | 6/2011 | Chelak |
| 2011/0139704 A1 | 6/2011 | Choi |
| 2011/0140896 A1 | 6/2011 | Menzel |
| 2011/0141116 A1 | 6/2011 | Dalesch |
| 2011/0152739 A1 | 6/2011 | Roncadi |
| 2011/0155657 A1 | 6/2011 | Collins |
| 2011/0160649 A1 | 6/2011 | Pan |
| 2011/0166507 A1 | 7/2011 | Childers |
| 2011/0168614 A1 | 7/2011 | Pouchoulin |
| 2011/0171713 A1 | 7/2011 | Bluchel |
| 2011/0189048 A1 | 8/2011 | Curtis |
| 2011/0208072 A1 | 8/2011 | Pfeiffer |
| 2011/0208106 A1 | 8/2011 | Levin |
| 2011/0213289 A1 | 9/2011 | Toyoda |
| 2011/0218475 A1 | 9/2011 | Brugger |
| 2011/0218487 A1 | 9/2011 | Shang |
| 2011/0226680 A1 | 9/2011 | Jonsson |
| 2011/0230814 A1 | 9/2011 | Kopperschmidt |
| 2011/0232388 A1 | 9/2011 | Butterfield |
| 2011/0237997 A1 | 9/2011 | Beden |
| 2011/0237998 A1 | 9/2011 | Wariar |
| 2011/0240537 A1 | 10/2011 | Ferrarini |
| 2011/0240555 A1 | 10/2011 | Ficheux |
| 2011/0269167 A1 | 11/2011 | Bene |
| 2011/0272337 A1 | 11/2011 | Palmer |
| 2011/0272352 A1 | 11/2011 | Braig |
| 2011/0275984 A1 | 11/2011 | Biewer |
| 2011/0284464 A1 | 11/2011 | Roncadi |
| 2011/0297593 A1 | 12/2011 | Kelly |
| 2011/0297598 A1 | 12/2011 | Lo |
| 2011/0297599 A1 | 12/2011 | Lo |
| 2011/0300010 A1 | 12/2011 | Jamagin |
| 2011/0300230 A1 | 12/2011 | Peterson |
| 2011/0303588 A1 | 12/2011 | Kelly |
| 2011/0303590 A1 | 12/2011 | Childers |
| 2011/0303598 A1 | 12/2011 | Lo |
| 2011/0309019 A1 | 12/2011 | Ahrens |
| 2011/0315611 A1 | 12/2011 | Fulkerson |
| 2011/0319823 A1 | 12/2011 | Bojan |
| 2012/0010554 A1 | 1/2012 | Vantard |
| 2012/0018377 A1 | 1/2012 | Tsukamoto |
| 2012/0018378 A1 | 1/2012 | Kelly |
| 2012/0022440 A1 | 1/2012 | Childers |
| 2012/0029324 A1 | 2/2012 | Akonur |
| 2012/0029937 A1 | 2/2012 | Neftel |
| 2012/0031826 A1 | 2/2012 | Childers |
| 2012/0035534 A1 | 2/2012 | Yu |
| 2012/0037550 A1 | 2/2012 | Childers |
| 2012/0043279 A1 | 2/2012 | Kelly |
| 2012/0065567 A1 | 3/2012 | Zarate |
| 2012/0075266 A1 | 3/2012 | Shimizu |
| 2012/0214117 A1 | 8/2012 | Broker |
| 2012/0259282 A1 | 10/2012 | Alderete |
| 2013/0126413 A1 | 5/2013 | Van Der Merwe |
| 2013/0140652 A1 | 6/2013 | Erdler |
| 2013/0184638 A1 | 7/2013 | Scarpaci |
| 2013/0199998 A1 | 8/2013 | Kelly |
| 2013/0220907 A1 | 8/2013 | Fulkerson |
| 2013/0233395 A1 | 9/2013 | Dinh |
| 2013/0292319 A1 | 11/2013 | Fulkerson |
| 2014/0199193 A1 | 7/2014 | Wilt |

FOREIGN PATENT DOCUMENTS

| | | |
|---|---|---|
| CN | 1235849 A | 11/1999 |
| CN | 1471617 A | 1/2004 |
| CN | 101175514 | 5/2008 |
| CN | 101269247 | 9/2008 |
| CN | 101311589 | 11/2008 |
| CN | 101801432 | 8/2010 |
| CN | 201600175 U | 10/2010 |
| CN | 101977642 | 2/2011 |
| CN | 102596283 A | 7/2012 |
| CN | 102639201 A | 8/2012 |
| CN | 103476486 A | 12/2013 |
| EP | 0121085 | 10/1984 |
| EP | 0121085 A1 | 10/1984 |
| EP | 0808633 | 11/1997 |
| EP | 2237814 | 10/2010 |
| GB | 1579177 | 11/1980 |
| JP | S50126866 A | 10/1975 |
| JP | S56138580 U | 10/1981 |
| JP | S5755010 U | 3/1982 |
| JP | S5913770 U | 1/1984 |
| JP | S59127978 U | 8/1984 |
| JP | S6037674 U | 3/1985 |
| JP | S60108870 | 6/1985 |
| JP | S60108870 U | 7/1985 |
| JP | S63202882 A | 8/1988 |
| JP | S63192912 U | 12/1988 |
| JP | H02114269 U | 9/1990 |
| JP | H0413143 U | 2/1992 |
| JP | 005176991 A | 7/1993 |
| JP | H05172268 A | 9/1993 |
| JP | H06230023 A | 8/1994 |
| JP | H07504507 A | 5/1995 |
| JP | H08511094 | 11/1996 |
| JP | H11137673 A | 5/1999 |
| JP | 2002119585 A | 4/2002 |
| JP | 2002139165 A | 5/2002 |
| JP | 2002523772 | 7/2002 |
| JP | 2003502091 | 1/2003 |
| JP | 2004057284 | 2/2004 |
| JP | 3126509 U | 11/2006 |
| JP | 2008055185 A | 3/2008 |
| JP | 2008291911 A | 4/2008 |
| JP | 2008511094 A | 4/2008 |
| JP | 2008531192 | 8/2008 |
| JP | 2008531192 A | 8/2008 |
| JP | 2008531192 A1 | 8/2008 |
| JP | 2009521965 | 6/2009 |
| JP | 2012510826 A | 5/2012 |
| MX | 20103880 | 7/2010 |
| TW | 200824731 A | 6/2008 |
| WO | 1980002806 | 12/1980 |
| WO | 9318380 A1 | 9/1993 |
| WO | 199318380 | 9/1993 |
| WO | 1993018380 A1 | 9/1993 |
| WO | 9420154 A1 | 9/1994 |
| WO | 9428386 A1 | 12/1994 |
| WO | 199428386 | 12/1994 |
| WO | 1996025214 | 8/1996 |
| WO | 1997027490 | 7/1997 |
| WO | 9823353 | 6/1998 |
| WO | 1999030757 A1 | 6/1999 |
| WO | 0021590 A1 | 4/2000 |
| WO | 20015069412 A1 | 7/2001 |
| WO | 2003099354 | 12/2003 |
| WO | 2003101510 A1 | 12/2003 |
| WO | 2004009158 A2 | 1/2004 |
| WO | 2005065126 A2 | 7/2005 |
| WO | 2005089832 A2 | 9/2005 |
| WO | 200609362 | 9/2006 |
| WO | 2006120415 | 11/2006 |
| WO | 2007028056 | 3/2007 |
| WO | 2007140241 A1 | 12/2007 |
| WO | 2008053259 A1 | 5/2008 |
| WO | 2008129830 A1 | 10/2008 |
| WO | 2009042181 A1 | 4/2009 |
| WO | 2009045589 A2 | 4/2009 |
| WO | 2009065598 | 5/2009 |
| WO | 2009073567 | 6/2009 |
| WO | 2009091963 | 7/2009 |
| WO | 2009157877 | 12/2009 |
| WO | 201042666 A2 | 4/2010 |
| WO | 2010042666 | 4/2010 |
| WO | 2010042667 | 4/2010 |

(56) References Cited

FOREIGN PATENT DOCUMENTS

| WO | 2010062698 | | 6/2010 |
|---|---|---|---|
| WO | 2010062698 | A2 | 6/2010 |
| WO | 2010081121 | | 7/2010 |
| WO | 2010081121 | A1 | 7/2010 |
| WO | 2010114932 | | 10/2010 |
| WO | 2012108910 | | 8/2012 |
| WO | 2014105267 | A1 | 7/2014 |
| WO | 2014105755 | | 7/2014 |

OTHER PUBLICATIONS

Anthony J. Wing et al., 'Dialysate Regeneration', Replacement of Renal Function by Dialysis, Chapter 17, 323-340 (William Drukker et al., eds., Martinus Nijhoff Publishers, 2nd ed., 1983).
CD Medical, Inc., 'Operator's Manual Drake Willock 480 Ultrafiltration Control Single Patient Delivery System', 1988.
Cobe Laboratories, Inc., 'CentrySystem 3 Dialysis Control Unit Operators Manual', Sep. 1988.
Fresenius AG, 'Acumen Acute Dialysis Machine Operating Instructions', Version 1.0, May 1996.
Manns et al., 'The acu-men: A New Device for Continuous Renal Replacement Therapy in Acute Renal Failure', Kidney International, vol. 54 (1998), 268-274.
NxStage Medical, Inc., 'NxStage System One User's Guide', Software Version 4.3, Part 1 through Part 6-20, 2006.
NxStage Medical, Inc., 'NxStage System One User's Guide', Software Version 4.3, Part 6-20 through Part C-17, 2006.
REDY 2000 Operator's Manual (1991) (Sorbent cartridge-based hemodialysis system).
REDY 2000 Service Manual (1989) (Sorbent cartridge-based hemodialysis system).
Renal Solutions, Inc., 'Dialysate Tubing Set and Dialysate Reservoir Bag for the Allient Sorbent Hemodialysis System', Instructions, 2004.
Renal Solutions, Inc., 510(K) for the SORB+ and HISORB+ Cartridges, Mar. 31, 2003.
Renal Solutions, Portions of the Allient Sorbent Hemodialysis System, Home User Manual, 2006, Chapters 1-3.
Reyes et al., 'Acid-Base Derangements During Sorbent Regenerative Hemodialysis in Mechanically Ventilated Patients', Critical Care Medicine, vol. 19, No. 4, 1991, 554-559 (col. 2, lines 17-22).
Seratron Dialysis Control System Operations Manual (cumulative 1980).
Ward et al., 'Sorbent Dialysis Regenerated Dialysis Delivery Systems', Peritoneal Dialysis Bulletin, Chapter 8, 3(2): S41-S48 (Apr.-Jun. 1983).
COBE Renal Care, Inc., "Sorbent Dialysis Primer", Edition 4, Sep. 1993.
Fresenius USA, Inc., "Fresenius 2008H Hemodialysis Machine", Part No. 490005, Revision H, 1994-2001.
International Search Report for PCT/US10/20698, Xcorporeal, Inc., Jun. 16, 2010.
Renal Solutions, Inc., Portions of 510(k) Allient Sorbent Hemodialysis System (Allient Main Controller Software Architecture Overview), Renal Solutions, Inc., Dec. 17, 2004.
Renal Solutions, Inc., Portions of 510(k) Allient Sorbent Hemodialysis System (Sections A-I), Dec. 17, 2004.
Renal Solutions, Inc., Portions of 510(k) Allient Sorbent Hemodialysis System (Sections M.3 and M.4), Renal Solutions, Inc., Dec. 17, 2004.
Renal Solutions, Portions of the Allient Sorbent Hemodialysis System, Home User Manual, 2006, Chapters 4.
Renal Solutions, Portions of the Allient Sorbent Hemodialysis System, Home User Manual, 2006, Chapters 5 to end.
Renal Solutions, Portions of the Allient Sorbent Hemodialysis System, Operator Manual, 2008, Chapter 3.
Renal Solutions, Portions of the Allient Sorbent Hemodialysis System, Operator Manual, 2008, Chapter 4, 4-1 to 4-33.
Renal Solutions, Portions of the Allient Sorbent Hemodialysis System, Operator Manual, 2008, Chapter 4, 4-34 to 4-69.
Renal Solutions, Portions of the Allient Sorbent Hemodialysis System, Operator Manual, 2008, Chapter 5.
Renal Solutions, Portions of the Allient Sorbent Hemodialysis System, Operator Manual, 2008, Chapters 1 to 2.
Renal Solutions, Portions of the Allient Sorbent Hemodialysis System, Operator Manual Model 1500, 2008, Chapter 3, 3-2 to 3-30.
Renal Solutions, Portions of the Allient Sorbent Hemodialysis System, Operator Manual Model 1500, 2008, Chapter 3, 3-31 to 3-70.
Renal Solutions, Portions of the Allient Sorbent Hemodialysis System, Operator Manual Model 1500, 2008, Chapters 1 to 2.
Renal Solutions, Special 510(k) Device Modification, Allient Sorbent Hemodialysis System, Mar. 15, 2007.

\* cited by examiner

VALVE SYSTEM

CROSS-REFERENCE

The present application is a continuation of U.S. patent application Ser. No. 12/351,969, entitled "Valve System", which was filed on Jan. 12, 2009.

FIELD

The present specification generally relates to the field of valves and more specifically to an electrically driven, magnetic valve for use in kidney dialysis systems where low power consumption, low heat generation, high reliability and a small, light size are functional requirements.

BACKGROUND

Valves are widely used to control the flow of fluids through systems. Valve requirements vary dramatically depending upon the nature and scope of the application. In a kidney dialysis system, particularly portable kidney dialysis systems, the functional requirements for a valve include low power consumption, low heat generation, high reliability and a small, light size.

Typically, automated valves in kidney dialysis systems require energy input to maintain at least one state, namely an open state or closed state. However, the on-going need for energy input to maintain a state has substantial disadvantages. First, the system requires a higher amount of energy, thereby decreasing system mobility. Second, a system failure can cause a cut off in energy supply, thereby adversely affecting the state of a valve and causing a major secondary system failure that can hurt a kidney dialysis patient.

Valves that operate between two states (open and closed) in which energy input is required to change a state, but not to maintain a state, are known. For example, U.S. Pat. Nos. 6,836,201, 5,322,258, 6,517,045, and 7,314,208 all of which are incorporated by reference, disclose valves in which energy input is required to change a state, but not to maintain a state. However, these valve systems have not been applied, or were suggested to be applied, to the field of kidney dialysis. Moreover, they are typically not suitable for reliably maintaining the valve's closed state at the size dimensions, reliability, and force levels required by kidney dialysis systems.

In sum, valves disclosed in the medical, and more specifically kidney dialysis, fields of art are not suitable to effectively meet the aforementioned functional needs. Accordingly there is need in the prior art for an improved valve with the aforementioned attributes.

SUMMARY

In one embodiment, the present specification is directed to a valve having an open position and a closed position comprising an orifice closing member adjacent to an orifice through which fluid can flow, a displacement member having a first portion and a second portion, wherein said first portion is adjacent to the orifice closing member when the valve is in said open position, a first magnet and a second magnet wherein said first and second magnets are sufficiently proximate to said displacement member to exert a magnetic force on said displacement member, and an actuator for generating a magnetic field to move said displacement member toward said first magnet, cause said first portion to press against the orifice closing member, and cause the orifice closing member to close said orifice.

Optionally, the first portion comprises a housing, compliant material, such as a spring, a rod and a gap between the compliant material and the rod. The valve further comprises an optical sensor positioned to sense if a gap in said valve is present or absent. The first portion comprises a rod and the second portion of the displacement member is a metal body with a diameter greater than said rod. The rod is bonded to said cylinder. The first magnet is larger than said second magnet. The orifice closing member comprises at least one of a diaphragm, an elastic material, a compliant material and a compressible material. The orifice is part of a manifold for a kidney dialysis system. The orifice closing member compresses against a valve seat to close said orifice. The valve seat is part of a manifold for a kidney dialysis system. The orifice closing member is part of a manifold for a kidney dialysis system.

In another embodiment, the valve comprises a) an orifice closing member adjacent to an orifice through which fluid can flow wherein said orifice closing member compresses against a valve seat when the valve is in a closed position, b) a moveable member that is physically movable relative to said orifice closing member wherein said moveable member moves from a first position when said valve is in an open position to a second position when said valve is in said closed position and wherein, in said second position, the moveable member presses against the orifice closing member to cause said orifice closing member to compress against the valve seat, c) a first magnet and a second magnet having a separation wherein said first magnet and second magnet generate a magnetic field in the separation and wherein said magnetic field has a direction; and d) an actuator capable of generating an electromagnetic force, wherein said electromagnetic force reverses the direction of said magnetic field.

Optionally, the valve further comprises an optical sensor positioned to sense if a gap is present or absent. The moveable member comprises a rod and a cylinder with a diameter greater than the rod, along with a compliant material, such as a spring. The first magnet is larger than the second magnet. The orifice closing member and valve seat are part of a disposable manifold for a kidney dialysis system.

In another embodiment, the valve comprises a) a diaphragm, b) a valve seat adjacent to the diaphragm, wherein, when the valve is in a closed state, said diaphragm compresses against the valve seat and causes a sealing of the orifice through which fluid can flow and wherein, when the valve is in an open state, the diaphragm does not compress against the valve seat, c) a displacement member comprising a rod bonded to a cylinder wherein said displacement member is moveable relative to the diaphragm, wherein the rod does not compress the diaphragm when the valve is in the open position, and wherein the rod compresses the diaphragm when the valve is in the closed position, d) a first magnet and a second magnet wherein the first magnet is larger than the second magnet, wherein the first magnet exerts a greater magnetic force on the cylinder than the second magnet when the valve is in the closed position and wherein the second magnet exerts a greater magnetic force on the cylinder than the first magnet when the valve is in the open position, and e) an actuator for generating the magnetic force exerted by said first magnet on said cylinder.

BRIEF DESCRIPTION OF THE DRAWINGS

These and other features and advantages of the inventions disclosed herein will be appreciated, as they become better understood by reference to the following detailed description when considered in connection with the accompanying drawings, wherein.

DETAILED DESCRIPTION

Figure 1:
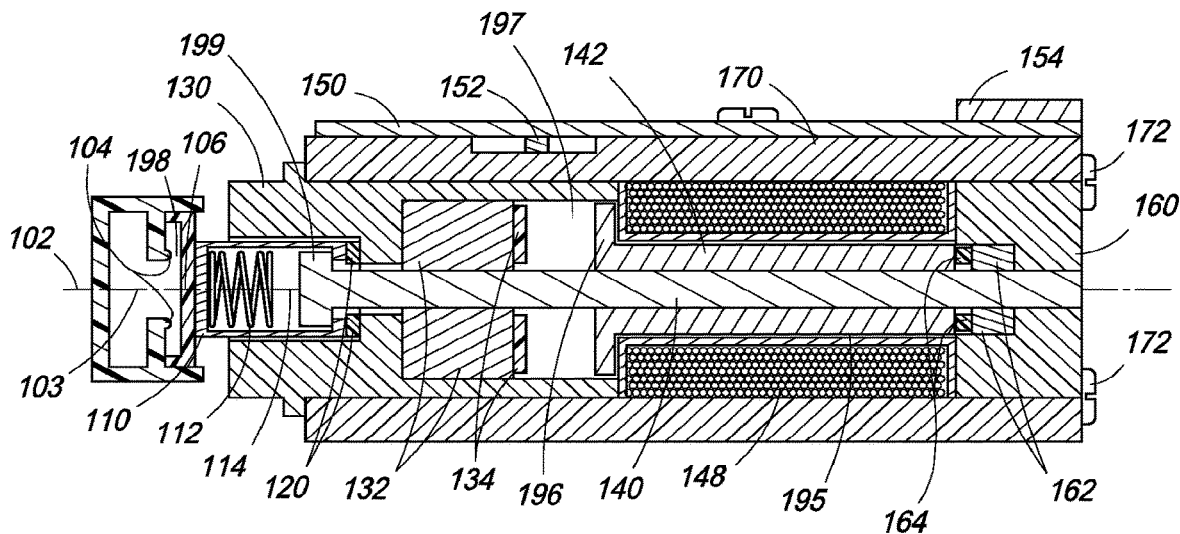
FIG. 1 depicts an embodiment of a valve of the present inventions where the valve is in an open state.

While the present specification may be embodied in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The present specification discloses a system that functions as a fluidic valve in a kidney dialysis system, such as a portable kidney dialysis system. The system comprises a magnetic displacement system that is lightweight and consumes minimum power, making it ideal even when the portable kidney dialysis system uses a disposable manifold for fluidic circuits. The system can be used in conjunction with an orifice in any structure. In particular, an orifice is any hole, opening, void, or partition in any type of material. This includes pathways in tubing, manifolds, disposable manifolds, channels, and other pathways. U.S. patent Ser. Nos. 12/324,924, 12/237,914, and 12/245,397, co-owned by the present applicant, disclose exemplary manifolds with which the present invention can be implemented and are incorporated herein by reference. One of ordinary skill in the art would appreciate that the presently disclosed valve system would be implemented with a disposable manifold by positioning the displacement member and magnets, as further discussed below, external to the manifold at the desired valve location. The actuator is also separate and distinct from the disposable manifold and generally part of the non-disposable portion of the kidney dialysis system.

Functionally, the valve has two stable states: open and closed. It operates by using magnetic forces to move a displacement member against a diaphragm and thereby create sufficient force to press the diaphragm against a valve seat and cause the diaphragm to close the orifice. Closing of the orifice shuts off fluid flow. The reverse process, namely the use of magnetic forces to move a displacement member away from the diaphragm and thereby release the diaphragm from compression against the valve seat, opens the orifice and permits fluid to flow.

Figure 2:
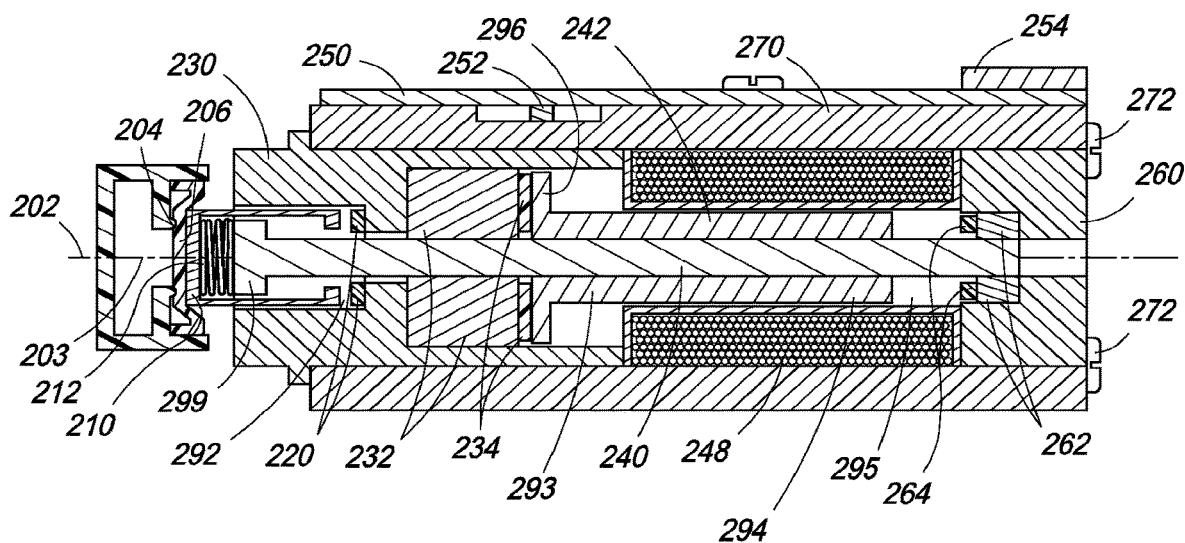
FIG. 2 depicts an embodiment of a valve of the present inventions where the valve is in a closed stated.
Figure 4:
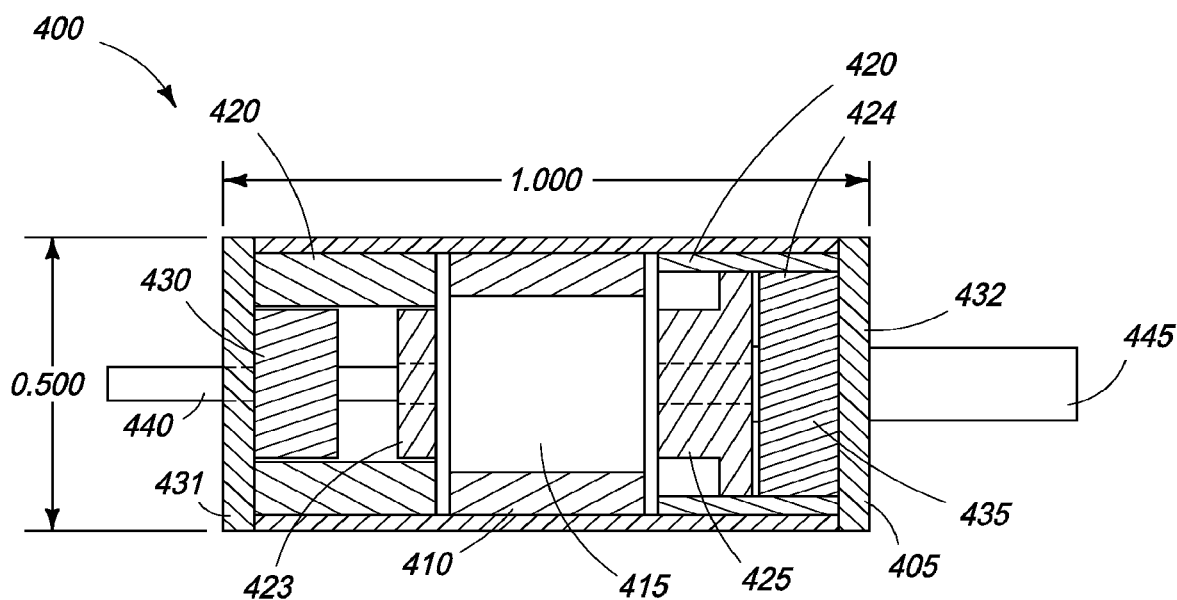
FIG. 4 shows a schematic diagram of another embodiment of a displacement member and mechanism of the present inventions.

It should be appreciated that while the inventions shall be discussed in terms of a preferred embodiment, depicted in FIGS. 1 and 2, and a non-preferred embodiment, depicted in FIG. 4, the present invention is generally directed to any use of a valve in a kidney dialysis system having the following attributes: a) two stable states, open and closed, b) changing states requires energy input, c) maintaining a state does not require energy input, d) a state is changed by the use of magnetic forces to modify the position of a displacement member which, when modified, causes a valve to either open or close.

In one embodiment, referring to FIG. 1, the valve system of the present invention 100 is used to control fluid flow through a fluidic flow channel 102, which is bounded by valve seats 104 to thereby create a valve annular orifice 103. As discussed above, orifice 101 is any hole, opening, void, or partition in any type of material, in particular, manifolds, disposable manifolds, channels, and other pathways 110. The valve 100 is shown in an open state. The components of the valve system include an orifice closing member, a displacement member, a mechanism for moving the displacement member, an optional optical sensor, a coil driver circuit, and an actuator having a coil.

In one embodiment, the orifice closing member comprises a diaphragm 106 which, when compressed by the displacement member, as discussed below, presses against the valve seats 104, thereby causing the valve annular orifice 103, to close. In an open state, the main body of the diaphragm 106 is separated from the valve seats 104 by a gap 198. In one embodiment, the diaphragm 106 is made from a soft material such as silicone rubber. The diaphragm 106 must maintain its shape over time, temperature, and actuations. The valve 100 relies upon the diaphragm material 106 to return to its uncompressed shape when the displacement member (compressing force) is removed, the open state.

One of ordinary skill in the art should appreciate that the orifice closing member can comprise any combination of spring, compressible, or non-compressible structures which, when pushed by the displacement member, closes the orifice. In one embodiment, the valve seats 104 can be molded into a manifold. Suitable materials for the valve seat are polycarbonate, ABS and similar plastics. The valve orifice 103 in the preferred embodiment ranges from 0.1 to 0.3 inches in diameter (and more particularly 0.190 inches). Orifice dimensions can be increased to increase flow for alternate applications of the invention or, alternatively, decreased to decrease flow for alternate applications.

In one embodiment, the displacement member comprises a plunger cap, or housing, 110, which, when the valve is in an open state, is aligned against the diaphragm 106, but not substantially compressing the diaphragm 106. Positioned inside the plunger cap 110 is a compliant component, such as a spring, 112 and the head of plunger 199, which are separated by an air gap 114. The plunger cap 110 is encompassed bound on the outside by a fluid seal 120, which in one embodiment, is a thin, soft silicone rubber washer. In one embodiment, the plunger cap 110 is forced against the silicone rubber washer and compresses the washer to form the fluid seal 120. When in a closed position, the plunger cap 110 is not forced against the washer, which is therefore not compressed and positioned loose to the end cap 130. The spring 112 is any elastic or compliant material and, in one embodiment, comprises a waves spring.

The plunger cap 110, internal spring 112, air gap, plunger head 199, plunger body 140, and core 142 are the components of the preferred displacement member of the present invention. In one embodiment, the plunger body 140 has an outer diameter in the range of 0.1 to 0.2 inches (more particularly 0.122 inches) and is approximately 0.5 to 2.5 inches long. It should be appreciated that the plunger body 140 is any rod structure of any length, depending on the application. The plunger body 140 is positioned within an annular core 142, which has one larger end and one smaller end, and is attached to the core via any method known to ordinary skill in the art, including epoxy, screw attachment, pinned, or welded. The outer diameter of the larger end of the core 142 is in the range of 0.3 inches to 0.5 inches (and more particularly 0.395 inches), the thickness is in the range of 0.03 to 0.15 inches (and more particularly 0.05 to 0.10), and the length is in the range of 0.50 to 1.75 inches long (and more particularly 1.05 inches). The small end of the core 142 has a diameter of 0.1 to 0.4 inches, and more particularly 0.25 inches.

At least partially encompassing the small end of the core is a coil bobbin 195, which keeps the coil 148 in place and provides dimensional stability to the coil 148. A gap preferably exists between the coil bobbin 195 and core 142. The size of the gap is approximately 0.01 to 0.03 inches (and more particularly 0.02 inches). The coil bobbin 195 is, in one embodiment, a glass filled nylon structure, which should be nonmetallic and non-ferromagnetic. The coil bobbin 195 is an annular structure with an outer diameter of a size sufficient to provide a tight fit into the housing bore and an inner diameter sufficient to enclose the core such that it has room to move and undergo some degree of thermal expansion. The two end caps 130, 160 wedge the bobbin 195 into place and keep it from moving or slipping, particularly when exposed to electromagnetic forces.

The plunger body is made of metal or non-metal material, such as brass or fiberglass, and the core is also made of metal, particularly steel 1018 or 1117. Preferably, the plunger body is non-magnetic and the core body is ferrous-magnetic. As discussed further below, the plunger body 140 and core 142 are moved by the mechanism for moving the displacement member, as further described below.

The mechanism for moving the displacement member comprises a large magnet component, a small magnet component and a housing within which the magnets and a portion of the displacement member, namely the plunger body 140 and core 142, are contained. More particularly, referring to FIG. 1, the mechanism to moving the displacement member comprises a large magnet end cap, to hold and align the large magnet, 130, a large magnet 132, an elastic material 134, a gap 197, a coil 148, a small magnet component 162, a small magnet mount and end cap 160, and an elastic material 164.

The large magnet end cap 130 holds and aligns the large magnet component 132 and coil bobbin 195 in place within a housing 170, referred to as the actuator body which has a borehole through which the components described herein are placed. The large magnet component 132 needs to be properly aligned with the core 142, plunger body 140, and small magnetic component 162 to ensure the proper movement of the displacement member. Both end caps 130 and 160 secure the coil bobbin 195 and coil 148 in position. Additionally, a mounting plate can be used to capture and hold end cap 130. In one embodiment, the mounting plate is positioned vertically and flush against the side of the end cap and between the end cap and bore. The mounting plate has a hole in it, roughly same size as the smaller diameter of the end cap. A clamping mechanism holds the body against the plate; alternatively the plate can be permanently fixed, using any boding technique known to persons of ordinary skill in the art. Unlike the prior art, such as U.S. Pat. No. 6,836,201, in a preferred embodiment, the magnets are located inside, not outside, the bore and provide bearings for the plunger, as discussed below.

The large magnet component 132 is separated from the core 142 by a gap 197 and elastic material 134, such as a silicone washer, which, in one embodiment, has an outer diameter of 0.3 to 0.5 inches (and more particularly 0.37 inches), an inner diameter of 0.1 to 0.3 inches (and more particularly 0.188 inches), a thickness of 0.005 to 0.015 inches (and more particularly 0.01 inches), and a durometer of 35 to 45 (and more particularly 40). The small magnet component 162 is separated from the core by an elastic material 164, such as a silicone washer, which, in one embodiment, has an outer diameter of 0.1 to 0.4 inches (and more particularly 0.24 inches), an inner diameter of 0.1 to 0.3 inches (and more particularly 0.188 inches), a thickness of 0.005 to 0.015 inches (and more particularly 0.01 inches), and a durometer of 35 to 45 (and more particularly 40). The small magnetic component 162 is held and kept properly aligned within the housing 170 by a small magnet mount and end cap 160. The small magnet end cap screws 172 also serve to capture and hold in place the small magnet end caps 160.

Referring to FIG. 1, the valve system of the present invention further comprises a coil driver circuit board 150, which drives the actuator, comprising coil 148, and is preferably mounted to the actuator body 170 via small screws, a coil driver connector 154, and an optical sensor 152, which senses the position of the large end of the core 196. Coil 148 serves to effectuate changes in magnetic fields in order to cause movement of the core 142 and plunger body 140. In one embodiment, the coil is approximately 0.05 to 1.5 inches long (and more particularly 1 inch long), has an outer diameter of 0.35 to 0.55 inches (and more particularly 0.46 inches), and an inner diameter of 0.15 to 0.35 inches (and more particularly 0.26 inches), with six layers of wire 29 AWG wire. The various elastic materials used in the displacement member and mechanism for moving the displacement member to provide a "soft" stop to the movement of the rod 140 when the valve opens or closes. In particular, it serves to ensure the movement of the core does not damage the magnets.

The large magnet component 132 can be one unitary magnet or, in a preferred embodiment, comprised of a plurality of magnets, such as three. The small magnet component 162 can also be unitary or comprised of a plurality of magnets. In one embodiment, the magnets are made of is preferably Alnico, Samarium Cobalt, Neodymium, Rare Earth, or Ceramic magnets. In one embodiment, the large magnet 132 is a Neodymium ring magnet with an outer diameter of 0.2 to 0.5 inches (and more particularly 0.375 inches), an inner diameter of 0.05 to 0.3 inches (and more particularly 0.125 inches), and a length of 0.2 to 0.5 inches (and more particularly 0.375 inches). In one embodiment, the small magnet 162 is made of Neodymium ring magnet, with an outer diameter of 0.15 to 0.4 inches (and more particularly 0.25 inches), an inner diameter of 0.05 to 0.3 inches (and more particularly 0.125 inches), and a length of 0.15 to 0.4 inches (and more particularly 0.25 inches). The larger magnet 132 is used closer to the orifice closing member because the size is necessary to generate sufficient opposition force to the valve seat. Further, the actuation force caused by the actuation coil is substantial equal even though the magnets are different size, thereby enabling a simple coil driver circuit.

In one embodiment, the rod, plunger or other elongated member 140 uses the magnets' center holes as a linear bearing. Accordingly, the magnets' center holes should preferably have a bearing surface, such as chrome or any smooth hard surface with minimal friction. A gap is placed between the coil bobbin 195 and the core 142 because of thermal expansion of the bobbin, bobbin creepage over time, and bobbin, core, and magnets tolerances. However, under all operating conditions, the gap should be sufficient such that the plunger body 140 can move freely and not bind in the openings of the magnets and coil. In a preferred embodiment, the gap is approximately 0.01 to 0.06 inches (and more particularly 0.02 inches) at room temperature.

When the valve is closed, referring to FIG. 2, the valve system of the present invention 200 controls fluid flow through a fluidic flow channel 202, which is bounded by valve seats 204, by compressing the orifice closing member, e.g. diaphragm 206, and thereby obstruct valve annular orifice 203. In a closed state, the main body of the diaphragm 206 is pressed against the valve seats 204 and, accordingly, substantially eliminates gap 198 (seen in FIG. 1).

Once just adjacent to the diaphragm 206, the displacement member now compresses the diaphragm 206. In particularly, plunger cap 210 has moved to compress the diaphragm 206. The plunger cap 210 has moved because a change in magnetic fields causes the core body 242 to move toward the large magnet component 232. The core body 242 stops moving when the core head 296 passes through the gap 197 (in FIG. 1) and stops at the elastic material 234 positioned adjacent to the large magnet component 232. Movement of the core 242 causes the plunger body 240, to which the core 242 is bonded, to move as well. Movement of the plunger body 240 causes the plunger head 299 to move within the plunger cap 210, pass through the gap 114 (in FIG. 1), and compress the spring 212. After a certain amount of compression, the plunger cap 210 moves and compresses the diaphragm 206. Movement of the plunger cap 210 creates a new gap 292 between the cap body 210 and the elastic material 220 that is positioned adjacent to the large magnet end cap 230.

As shown in FIG. 2, the other components of the valve remain the same, including the actuator body 270, coil driver circuit 250, coil connector 254, coil 248, coil bobbin 293, small end cap screws 272, optical sensor 252, small magnet end cap 260. It should be appreciated however, that, by virtue of the core 242 movement, a gap 295 is created between the smaller end of the core 294 and the elastic material 264, which is positioned adjacent to the small magnetic component 262.

It should be appreciated that, to close the valve, the displacement member applies a force to the orifice closing member, e.g. diaphragm 206. The force required, from the displacement member, to deform the diaphragm to the point where the diaphragm touches the valve seat is substantially linear and can be modeled as a linear spring. However, the force requirements increase exponentially as the diaphragm is compressed into the valve seat. Thus, the force profile for the displacement member becomes nonlinear and far more complex. Accordingly, there are several unique challenges associated with the design of the valve and the tolerances between the various components of the displacement member, the orifice closing member, and the hard stop of the displacement mechanism. The displacement mechanism must be able to deliver the nonlinear force profile without permanently deforming the diaphragm. This means that the mechanism must deliver just the right amount of force.

As discussed above, the displacement member comprises a rod, plunger or other elongated member that is bonded to another structure, referred to as a core, which has a larger diameter and can function as a stopper when forced up against another structure, such as a magnet face. One of ordinary skill in the art should appreciate that the displacement member or moveable member is not limited to a rod and cylinder configuration. On the contrary, it can include non-cylindrical structures, unitary pieces, or multiple pieces that are welded or, in any other manner, bonded together. In sum, the displacement member can comprise many different structures, provided the movement of the member can exert the requisite force on the orifice compressing member in a manner that is reliable and consistent.

For example, referring to FIG. 4, an alternate, less preferred embodiment is shown. For kidney dialysis applications, this embodiment does not typically reliably maintain the valve in a closed state. The displacement member 400 comprises a housing 405 that includes an electromagnet 410 with a substantially cylindrical structure and a borehole 415 running through it. The electromagnet 410 is securely positioned centrally within the housing 405 by non-magnetic spacers 420 which, in one embodiment are the end caps. The end caps have two purposes—hold the magnets in place and sandwich the coil in place. In one embodiment, elements 431 and 420 comprise a first unitary piece and 405 and 420 comprise a second unitary piece. A cylindrically shaped ferromagnetic core 425, having a first face 423 and a second face 424, is positioned to allow a portion of the core 425, between the first face 423 and the second face 424, to have a linearly slide-able fit with the bore 415. The second face 424 is sufficiently larger than the bore 415 thereby restricting the linear motion of the core 425. In one embodiment, the second face is differently sized relative to the first face to generate sufficient magnetic to keep the valve in a closed position. The core 425 is capable of left and right linear sliding motion within the bore 415.

Two differently sized magnets 430, 435 are also affixed within and at the two end caps 431, 432 of the housing 405. The first face 423 of the core 425 contacts with the first magnet 430 to form a first stable state of the displacement system 400 and the second face 424 of the core 425 contacts with the larger magnet 435 to form a second stable state of the displacement system 400. The placement of the permanent magnets 430, 435 is designed to be within the diameter of housing 405, as it reduces the size of the displacement system 400. A first rod 440 connected to the first face 423 of the core 425 passes through the first magnet 430 thereby protruding from the housing 405 at one end and a second rod 445 connected to the second face 424 of the core 425 passes through the second magnet 435 thereby protruding from the housing 405 at the other end. The rods 440, 445 can be made of non-corrosive, non magnetic, material known in the art, such as but not limited to, brass. While one embodiment has two rods connected to two faces of the core, in an alternate embodiment there is only one rod connected to one of the faces of the shuttle.

Persons of ordinary skill in the art would appreciate that the magnetic force exerted by the electromagnet 410 on the core 425 is sufficiently high to overcome the retention force of the permanent magnets 430, 435 so that the displacement system 400 can be changed from the first stable state to the second. Moreover, one of ordinary skill in the art would appreciate that the rod/plunger 445 moves with the core 425, thereby creating the motive force to compress or decompress the orifice closing member. However, this embodiment has been determined to be inferior to the first embodiment because it fails to sufficiently hold the closed state.

Several design features of the orifice closing member operating in conjunction with the displacement member and mechanism should be appreciated. First, referring to FIG. 5, and as discussed above in relation to FIGS. 1 and 2, a gap exists between the plunger cap 504 and the orifice closing member 505, in particular the first diaphragm face 505. The gap is in the range of 0.040 to 0.070 inches and more particularly approximately 0.055 inches. The diaphragm comprises silicone, preferably a thickness of 0.040 inches, and can be modeled as a spring ($K_{V2}$) having a spring constant of 270 lbf/in. The second diaphragm face 506 is separated from the valve seat 507 and acted upon by magnetic forces modeled as a spring, $K_{V1}$ having a spring constant of approximately 22.5 lbf/in and a thickness of approximately 0.047 inches.

The rod 504 translates the force generated by the magnetic attraction of the core 501 to the magnet 503 modeled by spring Kp, which is separated from the core head 501 by a washer, e.g. 0.010 inches of silicone in a closed state and is separated from core head 501 by approximately 0.110 inches in an open state. This silicone washer provides forces which are modeled as a spring, $K_{SL}$. The core 501 is bonded to the rod 504. When the valve is actuated, the rod 504 moves in the direction of the valve seat 507 because the core, to which the rod is bonded, moves in the direction of the large magnet 503.

Figure 5:
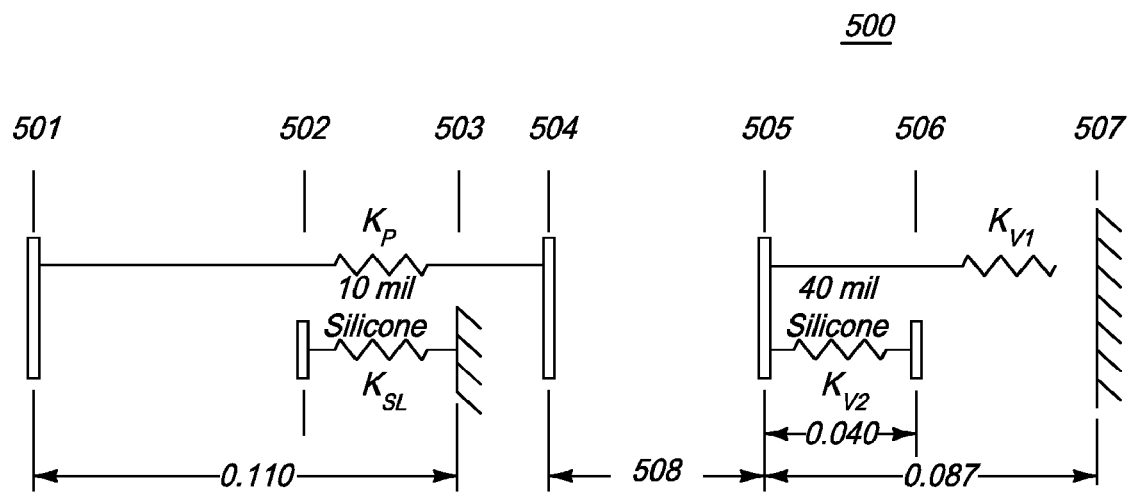
FIG. 5 is a schematic illustration of one embodiment of the displacement system of the present invention when the valve is in an open state.

Referring to FIG. 5, $K_{V2}$ and $K_{SL}$ correspond to elastic material, such as silicone, which are modeled as rigid springs. It should be appreciated that, when a valve is in a closed state, there are two positions of importance. First, is the position of the rod against the diaphragm and the second is the position of the core face against the large magnet. When the valve is closed, the rod is pressing on the valve diaphragm with enough force to resist at least 600 mmHg back pressure generated within the fluid passage of the kidney dialysis system. In this embodiment, fluid pressures can reach 2600 mmHg and this system is designed to maintain the diaphragm firmly pressed against the valve seat to seal the orifice up to and including 2600 mmHg.

Additionally, when the valve is closed, the core's large face is pulled close to, or directly against, the large magnet. The magnetic attraction of the core to the large magnet generates the force that the rod applies to the orifice closing member, e.g. diaphragm. To generate a consistent and reliable force, the spacing between the core face and the face of the large magnet must be consistent. Therefore, it is preferred to place an elastic material 502, 503 between the core face 501 and the magnet face 504. The elastic material has a nonlinear spring constant and will compress until the resultant forces for the elastic material equals the magnetic forces. When the rod applies force to the diaphragm via the core, the core will experience the resultant force. For a static condition to occur, the sum of these forces on the core must equal zero. Furthermore, the elastic material serves to protect the magnet face from chipping or breakage during actuation.

Figure 7:
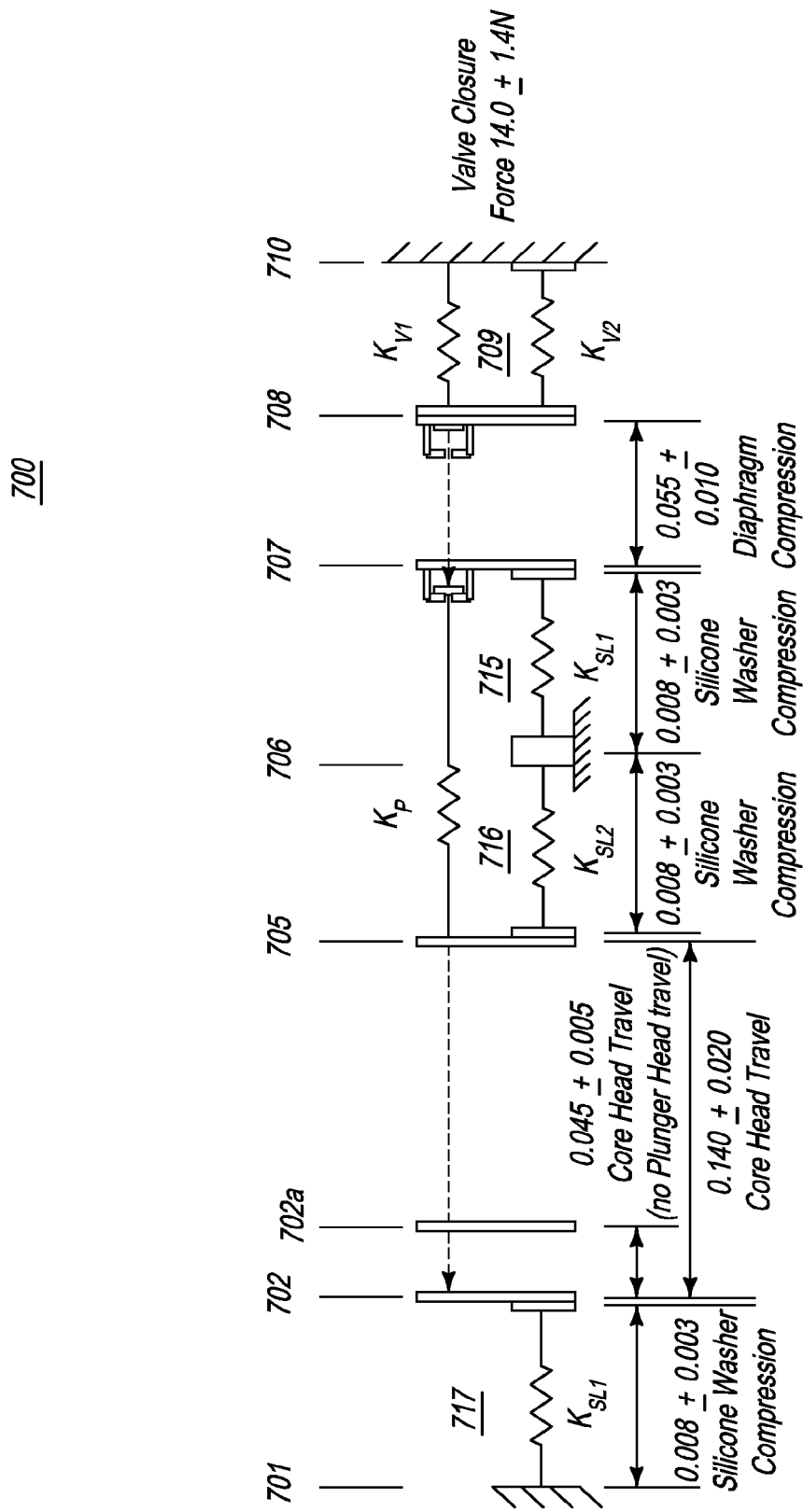
FIG. 7 is a schematic illustration of one embodiment of the displacement system of the present invention when the valve is in a closed state.

Referring to FIG. 7, when the valve 700 is in a closed state, the core head 705, 702 has moved away from the small magnet face 701 (from position 702a to position 702). When in position 702, the core head is separated from the small magnet 701 by an elastic material 717, such as a silicone washer having a thickness of approximately 0.015 inches. When in position 705, the core head will have moved approximately 0.140+/−0.20 inches, including a distance of 0.45+/−0.005 inches during which the rod 708 does not move, and stopped against an elastic material 716 (e.g. a silicone washer having a thickness of approximately 0.015 inches), which separates the core head 705 from the large magnet face 706. The large magnet 706 is, in turn separated from the rod head 707.

When the valve is in an open state, the large magnet 706 is separated from the rod head 707 by an elastic material 715, such as a silicone washer having a thickness of approximately 0.015 inches. When the valve is in a closed state, the large magnet 706 is separated from the rod head 707 by an elastic material 715, such as a silicone washer having a thickness of approximately 0.015 inches and a distance of approximately 0.055+/−0.10 inches. When the valve is closed, the rod head 707 has moved from being proximate to the large magnet 706 and elastic material 715 to being proximate to the valve seat 710. Specifically, the rod head 707 moves to compress the diaphragm 708 and thereby press against an elastic material 709 (e.g. silicone having a thickness of approximately 0.040 inches) which, in turn, presses against the valve seat 710. This causes the valve to close with an approximate force of 14 N.

Figure 6:
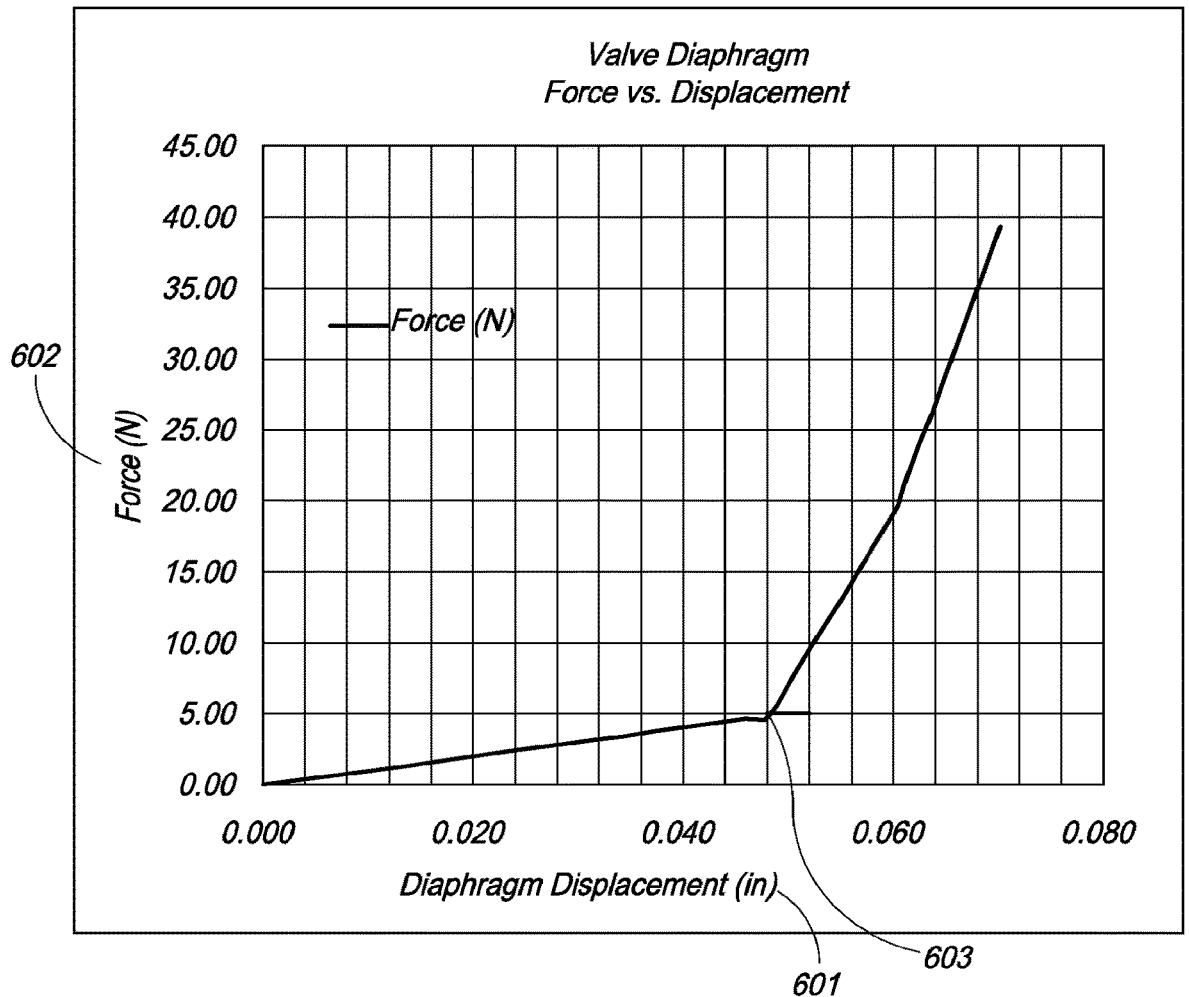
FIG. 6 is a chart showing an exemplary relationship between the force on one embodiment of an orifice compressing member and its displacement.

It should be appreciated that the configuration of the displacement member and mechanism relative to the orifice closing member and the tolerances described herein provide for a diaphragm displacement profile 600, as shown in FIG. 6 which is suitable for applications that need to resist at least 600 mmHg back pressure, such as kidney dialysis systems. Referring to FIG. 6, an exemplary diaphragm displacement profile is provided, where the force 602 exerted by the displacement member is provided on the y-axis and the corresponding diaphragm displacement is provided on the x-axis. The inflection point on this curve 603 indicates when the diaphragm starts being compressed against the valve seat. To the left of the inflection 603, the diaphragm is being forced to flex toward the valve seat, but there is no substantial compression against the valve seat. To the right of the inflection point 603, the diaphragm is flexed against the valve seat, deforming the diaphragm material and affecting a good seal against the fluid pressure.

Figure 3:
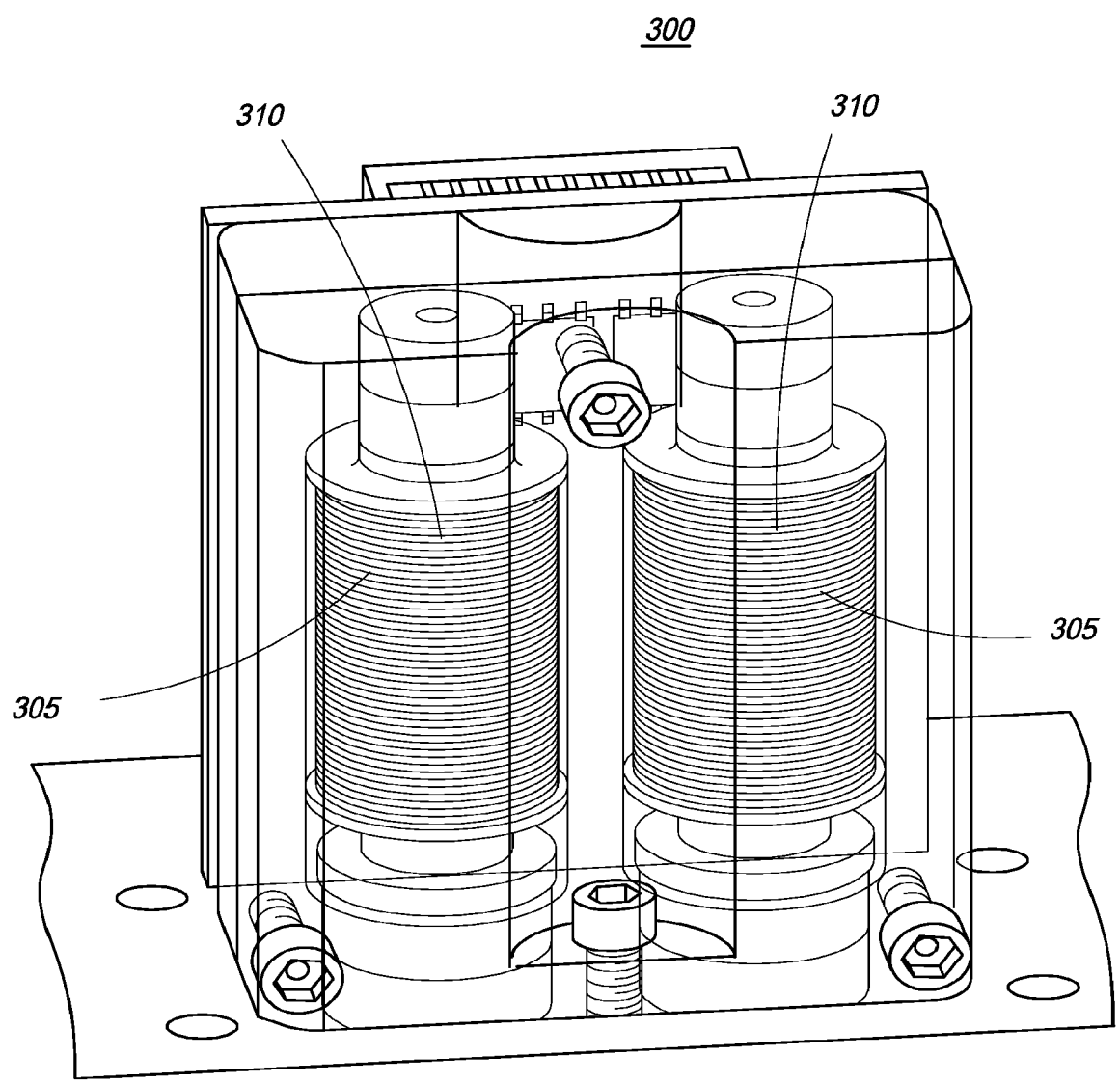
FIG. 3 is a diagram of one embodiment of the actuator.

Another important component of the displacement mechanism system is an actuator system. Referring to FIG. 3, during the actuation process, coils 305 are energized and the magnetic field builds, thus creating magnetic force opposing the small magnet attraction force. As the force builds, the core, discussed above, starts to move to the close position (large magnet). Once the core moves past a point of no return, the attraction forces on the core of the large magnet has overcome the attraction forces of the small magnet. To ensure that the opposing forces caused by the valve diaphragm do not overcome the attraction force of the large magnet, a gap is provided, as discussed above.

The coil design is made of coil form and magnet wire. The size of the coil form size is preferably based upon commercially available coil forms the pulsed current capability of the power supply, and, in particular, the required actuation force and the power supply voltage. The actuation force is proportional to the amp-turn rating of the coil. In one embodiment, it is preferred to limit the coil current to 6 amperes or less.

Factors important in the coil design include the number of layers, packing factor, wire diameter, and coil resistance. In one embodiment, the present invention uses a bobbin with 6 layers of wire and approximately 0.010 inches space between the bobbin flange diameter and the last layer. With an insulation requirement of heavy poly nylon and a coil resistance of 3.5+/−0.5 Ohms, the wire size is approximately 29 AWG. Any size coil form can be used.

The circuit used to drive the coil is an H-bridge circuit which enables current to be reversed for open and closed operations. The H-Bridge circuit is driven via a unique pulse width modulated (PWM) signal. The PWM signal is used to generate a cosine current pulse through the coil. The period of the cosine pulse is related to the mass of the core and the opposing force. The preferred embodiment does not use a bipolar DC power switch or sense switch; rather, the optical sensor operates to determine the position of the core, conclude the valve state, and generate an electronic drive cosine waveform to move the plunger in the desired direction, thereby changing the state of the valve.

Optionally, as shown in FIGS. 1 and 2 as elements 152, 252, the valve system uses a sensor, preferably an optical sensor, to determine the state of the valve (open or closed). This can be achieved by positioning the optical sensor in a location that has a sufficient difference in reflectivity, or other optical properties, between a valve open state and a valve closed state. For example, when the valve is closed, in one embodiment, the large end of the core 296 is positioned against an elastic material 234 and the large magnet component 232. The large end of the core 296 has a width wide enough to be sensed by a reflective optical sensor, but not too wide so the optical sensor has position resolution. The optical sensor will be placed on the outside of the displacement member/mechanism and look through its body, which is preferably made of transparent polycarbonate. The optical sensor's wavelength will be in the near infrared range (NIR) so as to have good transmission through the polycarbonate body. One of ordinary skill in the art would appreciate that the sensor can be chosen to suit any material structure, provided it includes the appropriate filters. Here, the optical sensor preferably has built into it a long pass optical filter for NIR responsivity.

Functionally, when the core is in the open position, as shown in FIG. 1, the large end of the core 196 moves out of the field of view of the optical sensor 152, thus very little reflection will be seen by the optical sensor. When the large end of the core 296 is in the field of view, as shown in FIG. 2, there will be a reflection that the sensor will see, thus indicating the core is in the closed position. One of ordinary skill in the art would appreciate that the sensor can be positioned such that it senses a great deal of reflectivity from the core when the valve is in the open position and much less reflectivity (because the core is moved out of the field of view) when the valve is in the closed position. Further, one of ordinary skill in the art would appreciate that the sensor could be positioned proximate to the gap to sense when the gap is present and when the gap is absent, thereby indicating the state of the valve.

Figure 8:
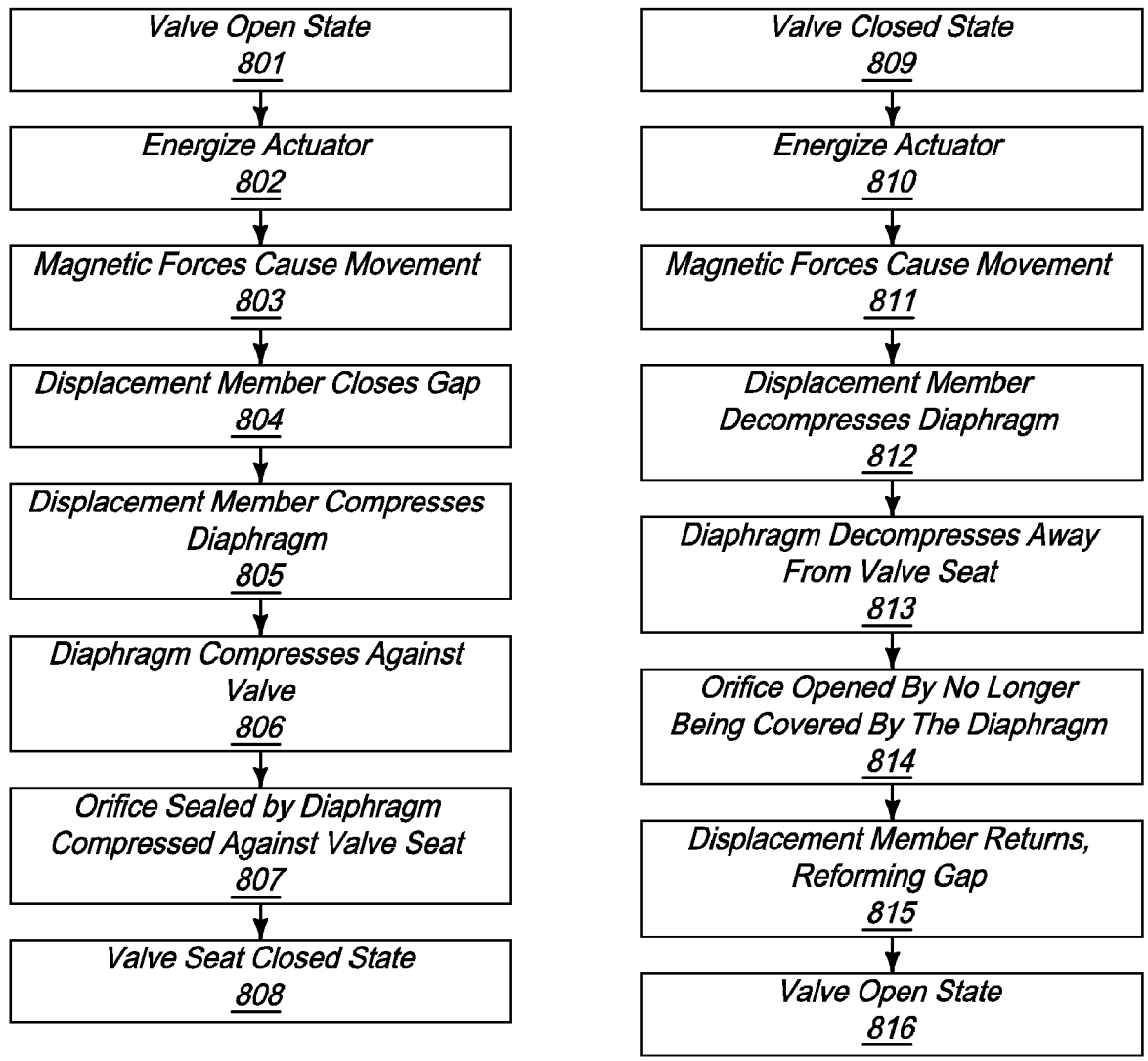
FIG. 8 is a flowchart describing steps for how the valve opens and closes.

Operationally, as referred to in FIG. 8, a valve is initially one of two states, open or closed. Assuming the valve is in an open state 801, the first step in closing the valve is to energize the coil driver circuit 802 and thereby cause the magnetic field generated by the coil to pass through the core, create an opposing magnetic force between the core and small magnet, and create a weak attraction force between the large magnet and the large end of the core. As the displacement member starts to move 803, the small magnet attraction force diminishes as the large magnet attraction forces increases. The displacement member moves 803 until a point of no return, after which the displacement member 804 closes a gap 804 and compresses the orifice closing member, namely the diaphragm 805, against the valve seat 806. The compression of the diaphragm 806 causes the diaphragm to close the orifice 807 and close the valve 808.

Referring to FIG. 8, assuming the valve is in a closed state 809, the first step in opening the valve is to energize the coil driver circuit 810 and thereby cause the magnetic field generated by the coil to pass through the core, create an opposing magnetic force between the core and large magnet, and create a weak attraction force between the small magnet and the small end of the core. As the displacement member starts to move 811, the large magnet attraction force diminishes as the small magnet attraction forces increases. The displacement member moves 811 until a point of no return, after which the displacement member decompresses the diaphragm 812 away from the valve seat 813. The orifice opens by virtue of no longer being covered by the diaphragm 814. The displacement member returns to its original position and recreate the gap 815.

Since the first and second stable states of the core are maintained even when power to the electromagnet is switched off, this allows for the displacement system to have low power consumption and low heat generation relative to prior art actuators where continuous power supply is needed to maintain states, additionally resulting in high heat generation.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

I claim:
1. A kidney dialysis system comprising:
a valve having a first state and a second state wherein:
the valve comprises a first magnet and a second magnet;
the valve comprises a displacement member positioned such that the first magnet and second magnet provide a bearing surface for movement of the displacement member;
the valve comprises elastic material positioned between a surface of the first magnet and the displacement member and positioned between a surface of the second magnet and the displacement member;
the valve is configured such that an input of energy into the valve modulates magnetic fields of the first magnet and the second magnet which cause the displacement member to move within the kidney dialysis system;
the movement of the displacement member causes a change between the first state and the second state; and
a maintenance of the first state or second state does not require energy input.
2. The kidney dialysis system of claim 1 further comprising: a disposable manifold having an orifice wherein the orifice is adapted to be closed to fluid flow when the valve is in the first state and wherein the orifice is adapted to be open to fluid flow when the valve is in the second state.

3. The kidney dialysis system of claim 2 wherein the valve comprises a compressible material and wherein the compressible material is configured to cover the orifice.

4. The kidney dialysis system of claim 3 wherein the movement of the displacement member compresses the compressible material into the orifice when the valve is in the first state.

5. The kidney dialysis system of claim 3 wherein the displacement member is configured such that the movement of the displacement member causes the compressible material to expand out of the orifice when the valve is in the second state.

6. The kidney dialysis system of claim 2 wherein the valve further comprises an orifice closing member, wherein the orifice closing member is configured to cover the orifice, and wherein the orifice closing member is configured to compress against a valve seat when the valve is in a closed position.

7. The kidney dialysis system of claim 6 wherein the displacement member is adapted to be physically movable relative to the orifice closing member, wherein the displacement member is adapted to move from a second position when the valve is in an open position to a first position and wherein, in the first position, the displacement member is adapted to press against the orifice closing member to cause the orifice closing member to compress against the valve seat.

8. The kidney dialysis system of claim 6, wherein the orifice closing member and valve seat are part of a disposable manifold for the kidney dialysis system.

9. The kidney dialysis system of claim 1, wherein the valve further comprises an actuator configured to generate capable of generating an electromagnetic force, wherein the electromagnetic force is adapted to reverse the direction of the magnetic fields.

10. The kidney dialysis system of claim 1, wherein the first magnet, having a first pole, is larger than the second magnet, having a second pole.

11. The kidney dialysis system of claim 10, wherein the first pole and second pole repel each other and wherein the first magnet and second magnet are configured to have the first pole and second pole face each other.

12. A kidney dialysis system comprising:
a disposable manifold having at least one orifice covered by a compressible material; and
a moveable displacement member positioned outside the disposable manifold and configured to move between a first state and a second state;
a first magnet and a second magnet positioned outside the disposable manifold and configured to provide a bearing surface for movement of the moveable displacement member; and
elastic material positioned between a surface of the first magnet and the moveable displacement member and positioned between a surface of the second magnet and the moveable displacement member, wherein the first magnet and second magnet generate ft magnetic fields, wherein an input of energy modulates the magnetic fields, and wherein maintenance of the first or the second state does not require energy input.

13. The kidney dialysis system of claim 12, wherein the orifice is positioned within a fluid pathway and wherein the fluid pathway is closed to fluid flow when the displacement member is in the first state and wherein the fluid pathway is open to fluid flow when the displacement member is in the second state.

14. The kidney dialysis system of claim 13 wherein the movement of the displacement member compresses the compressible material into the orifice when the displacement member is in the first state.

15. The kidney dialysis system of claim 13 wherein the movement of the displacement member valve causes the material to expand out of the orifice when the displacement member moves from the first state to the second state.

16. The kidney dialysis system of claim 12 wherein the compressible material compresses against a valve seat when the displacement member is in the first state.

17. The kidney dialysis system of claim 12, wherein the first magnet is larger than the second magnet.

18. The kidney dialysis system of claim 17, further comprising an actuator configured to generate an electromagnetic force, wherein said electromagnetic force is adapted to reverse the direction of the magnetic fields.

* * * * *